(12) United States Patent
Siev et al.

(10) Patent No.: US 6,787,612 B1
(45) Date of Patent: Sep. 7, 2004

(54) RESIN DERIVATIZATION METHOD AND USES THEREOF

(75) Inventors: Daniel V. Siev, San Diego, CA (US); J. Edward Semple, San Diego, CA (US); Michael I. Weinhouse, Escondido, CA (US)

(73) Assignee: Dendreon Corporation, Seattle, WA (US)

(*) Notice: Subject to any disclaimer, the term of this patent is extended or adjusted under 35 U.S.C. 154(b) by 13 days.

(21) Appl. No.: 09/122,576

(22) Filed: Jul. 24, 1998

(51) Int. Cl.$^7$ ............................ C08F 3/32; C08F 3/30
(52) U.S. Cl. ................ 525/375; 525/329.9; 525/330.5; 525/333.6; 525/376
(58) Field of Search ............................ 436/85; 528/492

(56) References Cited

U.S. PATENT DOCUMENTS

| | | | |
|---|---|---|---|
| 3,873,514 A | * 3/1975 | Chu et al. ...................... 536/3 |
| 4,874,813 A | * 10/1989 | O'Shannessy ............. 525/54.1 |
| 5,283,293 A | 2/1994 | Webb |
| 5,367,072 A | 11/1994 | Webb |
| 5,371,072 A | 12/1994 | Webb et al. |
| 5,492,895 A | 2/1996 | Vlasuk et al. |
| 5,514,777 A | 5/1996 | Webb et al. |
| 5,597,804 A | 1/1997 | Webb et al. |
| 5,637,599 A | 6/1997 | Levy et al. |
| 5,646,165 A | 7/1997 | Abelman et al. |
| 5,656,600 A | 8/1997 | Abelman et al. |
| 5,656,645 A | 8/1997 | Tamura et al. |
| 5,681,844 A | 10/1997 | Abelman et al. |
| 5,696,231 A | 12/1997 | Abelman et al. |
| 5,703,208 A | 12/1997 | Semple et al. |
| 5,714,580 A | 2/1998 | Brunck et al. |
| 5,731,413 A | 3/1998 | Webb et al. |
| 5,739,112 A | 4/1998 | Brunck et al. |

FOREIGN PATENT DOCUMENTS

WO    WO93/14779    8/1993

OTHER PUBLICATIONS

Carey, F. A.; Sundberg, R.J. Advanced Organic Chemistry 3rd Ed. New York: Plenum Press. 1990, pp. 146–147.*
Murphy, A. M.; Dagnino, R.; Vallar, P. L.; Trippe, A. J.; Serman, S. L.; Lumpkin, R. H.; Tamura, S. Y.; Webb, T.R. "Automated Synthesis of Peptide C–Terminal Aldehydes" J. Am. Chem. Soc. 1992, 114, 3156–3157.*
Galapin, I. J.; Beynon, R. J.; Cheland, J.; Mulligan, M. T.; Place, G. A. "A new approach to the synthesis of peptide aldehyde inhibitors" Peptides: Structure and Function: Proceedings of the Ninth American Peptide Symposium, 1985, Rockford, Illinois: 799–.*
R.M. McConnel, J.L. York, D. Frissell, C, Ezell, J. Med Chem 36: 1084–1089 (1993).
McConnell, R. M. et al., J. Med. Chem. 33: 86–93, 1990.
Kawamura et al., Chem. Pharm. Bull. 17: 1902, 1969.
Someno et al., Chem. Pharm. Bull. 34, 1748, 1986.
Westerik and Wolfinden, J. Biol. Chem., 247, 8195 (1972).
Ito et al., Chem. Pharm. Bull. 23, 3081 (1975).
Galpin, et al., Pept. Struct. Funct. Proc. Am. Pept. Symp., 9$^{th}$ 799–802 (1985), Edited by: Deber, C.M. Hruby, V.J., Kopple, K.D., Pierce Chem. Co., Rockford, Ill.
Murphy, A.M. et al., J. Am. Chem. Soc., 114: 3156 (1992).

* cited by examiner

*Primary Examiner*—Bennett Celsa
*Assistant Examiner*—Jon D. Epperson

(57) ABSTRACT

This invention provides a method for producing a derivatized resin useful in the arts of solid-phase peptide synthesis, combinatorial chemistry, and peptide or protein purification and separation. Methods for synthesizing the derivatized resin, the prototypical example of which is hydrazyl-carbonyl-amino methylated polystyrene, are provided by this invention disclosure.

16 Claims, No Drawings

RESIN DERIVATIZATION METHOD AND USES THEREOF

BACKGROUND OF THE INVENTION

1. Field of the Invention

This invention provides processes and methods for making derivatized resins useful in the arts of solid-phase peptide synthesis, combinatorial chemistry, peptide or protein purification and separation, and other arts. Resins prepared according to the method of this invention are solid support reagents suitable for use in conventional automated, semi-automated or manual peptide synthesis using protected amino acids or amino acid analogs, to give a protected peptide (or peptide analog) aldehyde or ketoamide, attached to the support reagent. The product peptide aldehyde or ketoamide peptide or peptide analog is cleaved from the support and deprotected to give the desired peptide or peptide analog in good yield. As opposed to known methods for peptide aldehyde or peptide ketoamide synthesis, the process of the present invention provides, among other benefits, a method for solid-phase peptide or peptide analog synthesis that minimizes the amount of solution-phase synthetic steps required.

2. Background

In the field of protease inhibition, a number of peptide and peptide analog inhibitors have been developed, as have methods for their synthesis (see U.S. Pat. Nos. 5,283,293; 5,367,072; 5,371,072; 5,492,895; 5,514,777; 5,597,804; 5,637,599; 5,646,165; 5,656,600; 5,656,645; 5,681,844; 5,696,231; 5,703,208; 5,714,580; 5,731,413; 5,739,112; all of which are herein incorporated by reference. Accordingly, there have been significant developments in the field of protease inhibition and the development of structure-activity profiles for a number of classes of protease inhibitors.

Of particular significance to the field of protease inhibition is the development of synthetic methods of ever increasing efficiency. Accordingly, there is a continued need in the art for efficient processes for solid-phase production of protease inhibitors and other peptidyl and peptidomimetic compounds. The present invention provides processes that are an improvement on existing solid-phase synthetic methods and resins.

In the art of protease inhibition, compounds including peptides, peptide analogs, and peptidomimetic compounds having an aldehyde group on the C-terminus of the peptide have been found to be good transition-state inhibitors, many of which show marked selectivity for specific proteolytic enzymes. However, significant difficulty has been encountered in the synthetic production of such molecules. Several methods for solution-phase synthesis of such compounds have been reported (see, for Example, U.S. Pat. No. 5,514,777 and references cited therein).

Methods for the solution-phase synthesis of peptide aldehydes have been reported. (McConnell, R. M. et al., J. Med. Chem. 33:86–93, 1990, and references cited therein; see also Kawamura et al., Chem. Pharm. Bull. 17:1902, 1969; Someno et al., Chem. Pharm. Bull. 34, 1748, 1986). The use of semicarbazides as aldehyde protecting reagents for the solution synthesis of peptide aldehydes has also been reported. (Westerik and Wolfinden, J. Biol. Chem., 247, 8195 (1972); Ito et al., Chem. Pharm. Bull. 23, 3081 (1975)). The use of soluble semicarbazide functionalized polymer has been reported for the manual preparation of some peptide aldehydes. (Galpin, et al., Pept. Struct. Funct. Proc. Am. Pept. Symp., 9th, 799–802, 1985, Edited by: Deber, C. M., Hruby, V. J., Kopple, K. D., Pierce Chem. Co., Rockford, Ill.). However such supports were reported not to be suitable for the automatic synthesis of peptide aldehydes, since they dissolve in the solvents used for the coupling steps.

The use of semicarbazone intermediates has been reported in the synthesis of peptidyl argininals. The unsubstituted semicarbazone, $N^g$-nitro-L-argininal semicarbazone was used as an intermediate in the synthesis of peptidyl argininals. McConnell, R. M., et al., J. Med. Chem., 33:86 (1990); R. M. McConnel, J. L. York, D. Frissell, C, Ezell, J. Med. Chem. 36:1084–1089 (1993). $N^g$-nitro-L-argininal semicarbazonyl-4-methylcyclohexane carboxylic acid was reported as an intermediate in the preparation of peptide aldehydes by a solid phase method. Murphy, A. M. et al., J. Am. Chem. Soc., 114:3156 (1992); and Webb, T. R., U.S. Pat. No. 5,283,293 (Feb. 1, 1994), and U.S. Pat. No. 5,367,072 (Nov. 22, 1994). $N^g$-nitro-L-argininal semicarbazonyl-4-diphenylmethane was reported as an intermediate for the solution-phase synthesis of peptidyl argininals. Brunck, T. K. et al., WO 93/14779 (1993). Solution and solid phase syntheses of peptidyl argininals was disclosed in U.S. Pat. No. 5,731,413 (Mar. 24, 1998). The disclosed methods implicated the use of an intermediate arginine cyclol N- or O-linked to a polymeric support.

The present invention provides a new method for the efficient production of argininal and other peptide or peptidomimetic aldehydes and ketoamides by solid phase synthesis, wherein a linkage between the aldehyde or ketoamide and a solid support provides for simplified chemistry with high yields of the desired product aldehyde or ketoamide. As opposed to known methods for peptide aldehyde synthesis, the process of the present invention provides a method for solid-phase peptide or peptide analog synthesis which provides the option of reduced reliance on solution-phase synthetic manipulation to produce desired aldehyde product. Accordingly, those skilled in the art will appreciate that the method of this invention represents a substantial contribution to the art in that solution-phase reactions, which may result in reduced product yield and which may require days if not weeks to accomplish, are accomplished according to the method of this invention within hours, due to reduced solution-phase synthetic chemistry heretofore required. By substantially reducing the product development cycle, true solid-phase combinatorial chemistry is enabled, including for heretofore difficult to synthesize, pharmacologically significant, aldehyde and ketoamide protease inhibitors.

SUMMARY OF THE INVENTION

Methods for synthesizing a derivatized solid support, the prototypical example of which is hydrazyl-carbonyl-amino methylated polystyrene (also referred to herein as "HCAM" resin or solid support), are provided by this invention. The processes according to this invention are used for preparing a functionalized solid support having the formula (I): la (I):

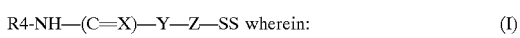

R4 is —NH—R3, —NH$_2$, —OH, or —O—R3, wherein R3 is a protecting group, provided that when R4 is —NH—R3 or —O—R3, then the protecting group is removed and replaced by —H in the final product (I);

X is O, S, or NR7;

R7 is H, alkyl, alkenyl, aryl, aralkyl, cycloalkyl, or heterocycle;

Y is absent, —NH—, or —CH$_2$—;

Z is absent or is a substituent selected from the group consisting of —NH—, —O—, —(C=O)—, —S—, SO$_2$—, alkyl, alkenyl, aryl, aralkyl, cycloalkyl, heterocycle, and combinations thereof, provided that when Y is absent and X is O or S, Z does not comprise —(C=O)— immediately adjacent to —(C=X)—, and when Y is —NH— and Z comprises an —NH— or an —S—, at least one carbon atom separates Y and the —NH— or —S— of Z, wherein, under conditions for peptide synthesis, functional groups of Z are protected; and SS is a solid support.

The derivatized solid support (I) is available for reaction at R4 with appropriately protected aldehyde or ketoamide moieties, extension of a peptide or peptide analog chain thereon, and subsequent cleavage thereof from the resin to yield free aldehyde or ketoamide product.

The product produced according to the methods of this invention is useful as a solid support for solid-phase peptide synthesis, combinatorial chemistry, the purification or isolation of peptides or proteins, and other uses.

Accordingly, it is one object of the present invention to provide a method whereby solid-phase peptide or peptidomimetic compounds comprising an aldehyde or ketoamide at the P1 position (i.e. the carboxy-terminal end) of the peptide or peptidomimetic compound is achieved, with reduced need for solution-phase synthetic manipulation.

A further object of this invention is to provide a method for derivatization of solid supports for use in solid-phase peptide synthesis.

A further object of this invention is to provide methods for derivatization of solid supports for use in combinatorial chemistry.

A further object of this method is to provide procedures for derivatization of solid supports for use in the purification or isolation of peptides or proteins.

Additional objects of this invention will become apparent from a review of the full disclosure, including the appended claims.

DETAILED DESCRIPTION OF THE PREFERRED EMBODIMENTS

1. Definitions

The present invention is directed to a method for production of derivatized solid supports, as well as methods of using the thus-derivatized solid supports in the arts of solid-phase peptide synthesis, combinatorial chemistry and peptide or protein purification and separation.

As used in this disclosure, the following terms have the defined meaning, unless expressly modified in the context in which the term is used:

SS is a polymeric solid support that is stable in the presence of acids, bases and/or other reagents; a "solid support" is any form of bead or resin typically used in the art of peptide synthesis to provide a "handle" whereby a growing synthetic peptide chain may be made available for synthetic manipulation without the risk of loss in peptide yield typically experienced when such syntheses are conducted in solution; the terms "solid support" and "resin" are used interchangeably. The term "solid support", "SS" or "support" refer to a solid particulate, insoluble material to which a linker moiety of the present invention is linked and from which a peptide or peptide analog may be synthesized. Supports used in synthesizing peptides and peptide analogs are typically substantially inert and nonreactive with the reagents used in the synthesis of peptides and peptide analogs, particularly once an initial linkage between an aldehyde or ketoamide has been established (i.e., a P1 position has been established), according to the method of this invention. Preferably, a solid support is a cross-linked resin, such as polystyrene.

NH$_2$—SS is a SS comprising at least one functional amino group available for formation of an amide (peptide) bond.

The term "amino acid" refers to natural amino acids or unnatural amino acids, and amino acid analogs in their D and L stereoisomers if their structure allows such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminoisobutyric acid, desmosine, 2,2'-diaminopimelic acid, 2,3-diaminopropionic acid, n-ethylglycine, N-ethylasparagine, hydroxylysine, all-hydroxylysine, 3-hydroxyproline, 4-hydroxyproline, isodesmosine, allo-isoleucine, N-methylglycine, N-methylisoleucine, N-methylvaline, norvaline, norleucine, ornithine and pipecolic acid. Amino acid analogs include, but are not limited to, the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone, aspartic acid-(beta methyl ester), N-ethylglycine, and alanine carboxamide.

The term "amino acid residue" refers to radicals having the structure (1) —NH—R—C(O), wherein R typically is —CH(R*)—, wherein R* is H or a carbon containing substituent; or

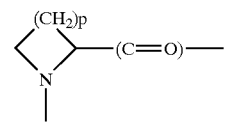

(2)

wherein p is 1, 2, or 3, representing the azetidinecarboxylic acid, proline or pipecolic acid residues, respectively.

A peptide or peptide analog is a molecule comprising at least two amino acids or amino acid analogs linked through peptide (amide) linkages.

A peptidomimetic compound is any compound which structurally resembles or mimics a natural peptidyl array, and compounds comprising such residues; compounds which, although not a natural peptide, in the sense that it either contains no amino acids or contains amino acid analogs, exhibits a biological activity of a known peptidyl compound.

The terms "good leaving group" or "leaving group" are used herein to define a molecular substituent which, when used in conducting chemical syntheses, exhibits the desirable properties of being labile under defined synthetic conditions, and of being easily separated from synthetic products under defined conditions. Examples of such leaving groups include, but are not limited to, hydrogen, hydroxyl radicals, halogen atoms, p-nitrophenoxide, water, methyl groups, and the like.

The term "protecting group" is used herein to refer to well known moieties which have the desirable property of preventing specific chemical reactions at a site on a molecule undergoing chemical modification intended to be left unaffected by the particular chemical modification, while at the same time being easily removed from the molecule under conditions that do not adversely affect other sites in the modified molecule. Those skilled in the art have a wide variety of known protecting groups to choose from, depending on the nature of the chemical site to be protected. Reference is made, for example, to "Protective Groups in Organic Synthesis", T. Greene, (John Wiley & Sons, Inc., 1991), and to "Solid Phase Peptide Synthesis," Stewart and Young (Pierce Chemical Co., 1984), herein incorporated by reference for this and other purposes. Examples of In protecting groups known in the art include, but are not limited to, Cbz, Boc, Alloc, Fmoc, Troc, Teoc ($Me_3Si(CH_2)_2OCO$), PMC, and the like, and others disclosed herein.

The term "alkyl" refers to saturated aliphatic groups including straight-chain, branched-chain and cyclic groups.

The term "alkenyl" refers to unsaturated aliphatic groups having at least one double bond.

The term "aryl" refers to aromatic groups which have at least one ring having a conjugated pi electron system and includes carbocyclic aryl, heterocyclic aryl and biaryl groups, all of which may optionally be substituted with a substituent selected from, but not limited to, lower alkyl of one to ten carbon atoms; alkenyl; nitro; cyano; halo; —$S(O)_q$—, wherein, for purposes of this definition, q is 0, 1, or 2; carboxylic acid or carboxylic acid derivatives, esters amides, and the like.

The term "aralkyl" refers to an alkyl group substituted with an aryl group. Exemplary aralkyl groups include, but are not limited to, benzyl, picolyl, and the like, which may optionally be substituted with a substituent selected from, but not limited to, lower alkyl of one to ten carbon atoms; alkenyl; nitro; cyano; halo; —$S(O)_q$—, wherein, for purposes of this definition, q is 0, 1, or 2; carboxylic acid or carboxylic acid derivatives, esters amides, and the like.

The term "cycloalkyl" refers to an alkyl in which at least a portion of the molecule is in a closed ring configuration. Exemplary cycloalkyl groups include, but are not limited to, cyclohexyl, cyclopropyl, cyclopentyl and cycloheptyl.

The term "heterocycle" refers to any compound having a closed cyclic structure in which at least one atom thereof is other than a carbon atom. For example, cyclic alkyl, cyclic aryl, cyclic aralkyl compounds containing a nitrogen, oxygen or sulfur atom in the cyclic structure are heterocycles.

The term "halo" or "halogen" refers to fluorine, chlorine, bromine and iodine.

The term "non-adverse conditions" describes conditions of reaction or synthesis which do not substantially adversely affect the skeleton of the peptide analog and/or its amino acid (and/or amino acid analog) components. One skilled in the art can readily identify functionalities, coupling procedures, deprotection procedures and cleavage conditions which meet these criteria.

A semicarbazone is a derivative formed by the reaction of a semicarbazide with an aldehyde or ketone of the general formula R'(R')C=NNH(CO)NHR'R', wherein for each occurrence of R', the R' is independently selected to be one of H, alkyl, aryl, and other organic residues, such as, for purposes of this invention, a solid support, an amino acid, a peptide or peptide analog.

A semicarbazide is a reagent of the formula $H_2NNH(CO)NH_2$ or a derivative thereof of formula $H_2NNH(CO)NR'R'$, which is known to react with a variety of electrophiles, including carbonyl compounds such as aldehydes and ketones, wherein for each occurrence of R', the R' is independently selected to be one of H, alkyl, aryl, and other organic residues, such as, for purposes of this invention, a solid support, an amino acid, a peptide or peptide analog.

Alloc is allyloxycarbonyl

Alloc-Cl is allyl chloroformate

A.M. resin is amino-methylated polystyrene resin

Boc is tert-butyloxy carbonyl or tert-butoxycarbonyl

Bom is benzyloxymethyl

BOP is benzotriazole-yl-oxy-tris-(dimethylamino) phosphonium hexafluorophosphate Cbz is benzyloxycarbonyl or carbobenzyloxy 2-Clz is 2-chlorobenzyloxycarbonyl DCM is dichloromethane DIEA is N,N-diisopropylethylamine DMF is N,N-dimethylformamide DMSO is dimethylsulfoxide EDC is 1-ethyl-3-(3-dimethylaminopropyl)carbodiimide hydrochloride salt Fmoc is 9-fluorenylmethyloxycarbonyl HCAM is hydrazyl-carbonyl-amino methylated polystyrene HF is hydrogen fluoride HOBT or HOBt is 1-hydroxybenzotriazole monohydrate HPLC is high pressure liquid chromatography; high performance liquid chromatography LAH is lithium aluminum hydride MS is mass spectrometry Mts is mesitylene-2-sulphonyl NMM is N-methylmorpholine (also referred to as 4-methylmorpholine)

NMR is nuclear magnetic resonance spectroscopy

PG is protecting group

PMC is 2,2,5,7,8-pentamethylchroman-6-sulfonyl

PyBOP is Benzotriazole-yl-oxy-tris-pyrrolidino-phosphonium hexafluorophosphate (Ph3P)4Pd is tetrakis-(triphenylphosphine)palladium(0)

r.t. or RT is room temperature

TBTU is 2-(1H-benzotriazole-1-yl)-1,1,3,3-tetramethyluronium tetrafluoroborate

TeOC is $Me_3Si(CH_2)OCO$

TFA is trifluoroacetic acid

THF is tetrahydrofuran

TLC or tlc is thin layer chromatography

TFMSA is trifluoromethylsulfonic acid, also commonly referred to as "triflic acid"

TMSOTf is trimethylsilyltrifluoro methane sulfonate

Tos is p-toluenesulfonly, also referred to as Tosyl or Ts

Troc is trichloroethoxycarbonyl (an amine protecting group removable with zinc)

NMR designations:

s is singlet d is doublet m is multiplet br is broad peak t is triplet q is quartet

2. Description of the Preferred Embodiments

According to the present invention, synthetic methods are provided for production of derivatized resin, also referred to as a derivatized solid support, and production of peptide or peptidomimetic products using those resins. From the present disclosure, it will be apparent that the methods disclosed herein are useful for the synthesis of peptides, peptide analogs, and peptidomimetics, and while all of these possibilities may not be recited in a particular context, production of all of these possibilities is intended. The method according to this invention comprises the steps of:

A. Preparing a Derivatized Resin Optimized for Reaction with Appropriately Protected Aldehyde or Ketoamide Moieties, wherein Said Resin is Represented by the Formula (I):

$$R4\text{-}NH\text{—}(C\text{=}X)\text{—}Y\text{—}Z\text{—}SS \text{ wherein:} \quad (I)$$

R4 is —NH—R3, —NH$_2$, —OH, or —O—R3, wherein R3 is a protecting group, provided that when R4 is —NH—R3 or —O—R3, then the protecting group is removed and replaced by —H in the final product (I);

X is O, S, or NR7;

R7 is H, alkyl, alkenyl, aryl, aralkyl, cycloalkyl, or heterocycle;

Y is absent, —NH—, or —CH$_2$—;

Z is absent or is a substituent selected from the group consisting of —NH—, —O—, —(C=O)—, —S—, SO$_2$—, alkyl, alkenyl, aryl, aralkyl, cycloalkyl, heterocycle, and combinations thereof, provided that when Y is absent and X is O or S, Z does not comprise —(C=O)— immediately adjacent to —(C=X)—, and when Y is —NH— and Z comprises an —NH— or an —S—, at least one carbon atom separates Y and the —NH— or —S— of Z, wherein, under conditions for peptide synthesis, functional groups of Z are protected;

SS is a solid support; and

B. Reacting an Aldehyde or Ketoamide with the Derivatized Resin of Step (A), thereby Producing an Immobilized Aldehyde or Ketoamide.

It will be appreciated that, by virtue of immobilization, the aldehyde or ketoamide may be purified or isolated from a solution and, optionally, subsequently released as the free aldehyde or ketoamide. Alternatively, solid-phase chemical modification of said immobilized aldehyde or ketoamide, including but not limited to solid-phase peptide synthesis thereon or combinatorial chemistry, may be conducted. Accordingly, the process of this invention may further comprise the additional steps of:

C. Optionally Performing Solid-phase Chemistry on the Immobilized Aldehyde or Ketoamide of Step (B), Selected from Peptide Synthesis, Synthesis of Peptide Analogs, and Combinatorial Chemistry, thereby Producing a Modified Aldehyde or Ketoamide.

Finally, the free aldehyde or ketoamide, modified or not, may be released from the resin by cleavage therefrom. Therefore, the method of this invention may further comprise the step of:

D. Cleaving, Deprotecting and Recovering the Aldehyde or Ketoamide of Step (B) or the Modified Aldehyde or Ketoamide of Step (C) as the Free Aldehyde or Ketoamide.

These aspects of the invented process are described in greater detail below:

A. Preparing a Derivatized Resin (I) Optimized for Reaction with Appropriately Protected Aldehyde or Ketoamide Moieties:

a. The Derivatized Resin Produced According to the Methods of this Invention:

The invention according to the present disclosure comprises the production of derivatized resins for use in any of a number of different methods, including solid-phase peptide synthesis, combinatorial chemistry and peptide or protein purification or isolation.

For reaction with appropriately protected aldehyde or ketoamide moieties, the methods of this aspect of the invention produce a functionalized solid support represented by formula (I):

$$R4\text{-}NH\text{—}(C\text{=}X)\text{—}Y\text{—}Z\text{—}SS \text{ wherein:}$$

R4 is —NH—R3, —NH$_2$, —OH, or —O—R3, wherein R3 is a protecting group, provided that when R4 is —NH—R3 or —O—R3, then the protecting group is removed and replaced by —H in the final product (I);

X is O, S, or NR7;

R7 is H, alkyl, alkenyl, aryl, aralkyl, cycloalkyl, or heterocycle;

Y is absent, —NH—, or —CH$_2$—;

Z is absent or is a substituent selected from the group consisting of —NH—, —O—, —(C=O)—, —S—, SO$_2$—, alkyl, alkenyl, aryl, aralkyl, cycloalkyl, heterocycle, and combinations thereof, provided that when Y is absent and X is O or S, Z does not comprise —(C=O)— immediately adjacent to —(C=X)—, and when Y is —NH— and Z comprises an —NH— or an —S—, at least one carbon atom separates Y and the —NH— or —S— of Z, wherein, under conditions for peptide synthesis, functional groups of Z are protected;

SS is a solid support.

b. Reactants and Synthetic Routes for Production of the Derivatized Resin of Formula (I):

The solid support of formula (I) is prepared by any of the following synthetic routes, wherein reactants as defined below are utilized. Each of these reactants is either readily available from commercial sources or may be prepared by those of ordinary skill in the art using standard synthetic methods, coupled with the disclosure and guidance provided herein. The reactants utilized have the following formulae and substituent definitions, wherein the reactant name or definition associated with a given reactant may be used to refer both to the generic formula thereof as well as to specific embodiments thereof. Alternatively, in certain instances, a species of a generic reactant may be given an new designation for clarity. In the following reactant definitions, variables defined above in the definition of the derivatized resin (I) have the same definitions below, unless otherwise specified:

(A) R—Y—Z—SS, wherein R is a leaving group.

(B) R1-(C=X)—R2, wherein R1 and R2 are independently selected leaving groups, same or different.

(C) R1-(C=X)—Y—Z—SS, wherein all variables are as defined above. This reactant (C) includes but is not limited to a commercially available carboxylated resin of formula:

HOOC—Y—Z—SS, and is prepared by carboxylating a commercially available resin bearing at least one functional amino group according to methods known in the art.

(D) R4-NH$_2$, wherein R4 is as defined above.

(E) R4-NH—(C=X)—R2, wherein all variables are as defined above.

(F) R4-NH—(C=X)—NH—Q, wherein Q is —R9–R10, wherein R9 is substituted or unsubstituted, alkyl, alkenyl, aryl, aralkyl, cycloalkyl and heterocycle, and R10 is a functional group selected from the group consisting of —NH$_2$, —OH, —COOH, —COCl, —SH, —SO$_2$Cl, —SO$_2$H, —SO$_3$-lower alkyl, provided that the terminal hydrogen, halogen or a reactive moiety of R10 may be replaced or protected by a protecting group, —R8, and moiety Q is selected such that the terminal substituent thereof is reactive with the terminal substituent of T within reactant (G), permitting bond formation between (G) and (F), upon contact thereof.

(G) T—Z—SS, wherein T is —CH$_2$Cl, —NH$_2$, or —COOH.

(H) NH$_2$—R7, wherein R7 is as defined above.

(J) R4-NH—(C=O)—NH—Q—R8, wherein all variables are as previously defined.

(K) R4-NH—(C=O)—NH—Q, wherein all variables are as previously defined.

(L) R4-NH—(C=S)—NH—Q—R8, wherein all variables are as previously defined.

(M) R4-NH—(C—S—R11)—Q—R8, wherein all variables are as previously defined.

(N) NH$_2$—Q—R8, wherein Q and R8 are as previously defined.

(P) R1-(C=X)—NH—Q—R8, wherein all variables are as previously defined.

(U) R4-NH—(C=X)—NH—Q—R8, wherein all variables are as previously defined.

(W) HOOC—NH—Q—R8, wherein all variables are as previously defined.

(AA) R4-N=C=X, an isocyanate when X is oxygen; a thiocyanate, when X is sulfur, and a carbodiimide, when X is N—R7.

(BB) (—)Y—Z—SS, an anion.

Synthetic Route 1:

Synthetic Route 1 for production of the derivatized resin of formula (I):

R4-NH—(C=X)—Y—Z—SS     (I)

comprises the steps of:

(i) reacting a starting material of formula

R—Y—Z—SS     (A)

with a reactant of formula

R1-(C=X)—R2     (B)

to form an intermediate product of formula

R1-(C=X)—Y—Z—SS;     (C)

(ii) reacting the intermediate (C) with a reactant of formula

R4-NH$_2$     (D)

to form the product (I) of formula R4-NH—(C=X)—Y—Z—SS; and (iii) recovering the product (I).

Synthetic Route 2:

Synthetic Route 2 for production of

R4-NH—(C=X)—Y—Z—SS     (I)

comprises the steps of:

(i) reacting a starting material of formula

R1-(C=X)—R2     (B)

with a reactant of

R4-NH$_2$     (D)

to form an intermediate of formula

R4-NH—(C=X)—R2;     (E)

(ii) reacting intermediate (E) with a reactant of formula

R—Y—Z—SS     (A)

to form the product (I) of formula R4-NH—(C=X)—Y—Z—SS; and (iii) recovering the product I.

Synthetic Route 3:

Synthetic route 3 for production of

R4-NH—(C=X)—Y—Z—SS     (I)

comprises the steps of:

(i) reacting a starting material of formula

R4-N=C=X,     (AA)

with the an anion of formula (BB):

(—)Y—Z—SS,     (BB)

and quenching the reaction with a proton source to form the product (I).

For carrying out this embodiment of the invention, it will be appreciated that a wide variety of proton sources may be employed, including but not limited to strong or weak acids, such as water, HCl, acetic acid and the like. In reactant (AA), where X is oxygen, an isocyanate reactant is utilized. Where X is sulfur, an appropriate thiocyanate is utilized, and where X is N—R7, a commercially available carbodiimide is employed.

The anion Y(—) in reactant (BB) is generated to permit reaction with reagent (AA) according to methods known in the art for anion, including carbanion, generation, including but not limited to treatment with an appropriate base. For this purpose, the base may be selected from the group consisting of: sodium or potassium hydride, sodium potassium or lithium alkoxide (e.g. ethoxide), potassium tert-butoxide, lithium diisopropyl amide, lithium or potassium bis(trimethylsilyl)amide, and the like.

Synthetic Route 4:

Synthetic route 4 for production of

R4-NH—(C=X)—NH—Z—SS     (IA)

comprises the steps of:

(i) reacting a starting material of formula:

T—Z—SS     (G)

with a reactant of formula:

R4-NH—(C=X)NH—Q; (F)

to form the product (IA);

(ii) recovering the derivatized resin (IA).

The reactant (F) of formula:

R4-NH—(C=X)—NH—Q; (F)

is prepared by a process comprising:

(i) reacting a starting material (N) of formula:

H$_2$N—Q—R8 (N)

with a reactant (B) of formula:

R1-(C=X)—R2 (B)

to form an intermediate (P) of formula:

R1-(C=X)—NH—Q—R8; (P)

(ii) reacting intermediate (P) with reactant (D) of formula

R4-NH$_2$ (D)

to form an intermediate (U) of formula:

R4-NH—(C=X)—NH—Q—R8; and (U)

(iii) removing R8 to form reactant (F);

wherein all variables are as previously defined.

Depending on the nature of the functional group(s) comprising Q, those skilled in the art will appreciate that the nature of the protecting group —R8 may need to be varied, (see the discussion below which describes preferred combinations of protecting groups and functional groups, as well as methods of deprotection). Accordingly, —R8 may be the same or different than —R3.

c. Embodiments and Variations on Synthetic Routes 14 for Production of the Derivatized Resin (I) of Formula R4-NH—(C=X)—Y—Z—SS:

Various embodiments of the invented synthetic routes described above include the following methods, the specifics of which are dictated by the desirable properties of the final product (I), including the desired character of the variables R4, X, Y and Z.

Thus, for example, an embodiment of Synthetic Route 1, wherein Y is selected to be —NH—, produces a product, referred to as (IA), by a process, process (IA), which comprises the steps of:

(i) reacting a starting material of formula:

NH$_2$—Z—SS (B)

with a reactant of formula:

R1-(C=X)—R2, (B)

wherein R1 and R2 are independently selected leaving groups that may be the same or different, to form the intermediate (C) of formula:

R1-(C=X)—NH—Z—SS; (C)

(ii) reacting the intermediate (C) with a reactant of formula:

R4-NH$_2$ (D)

to form the product (IA); and (iii) recovering the product (IA).

It will be appreciated that the following specific embodiments of Synthetic Routes 1–4 may be conducted as follows:

When Y is selected to be absent or —CH$_2$—, and X is O, a product referred to as (IB) is prepared by process (IB) comprising the steps of:

(i) reacting a starting material of formula:

R1-(C=X)—Y—Z—SS, wherein R1 is —OH, and X is O, (C)

with a reactant of formula:

R4-NH$_2$ (D)

to form the product (IB) of formula:

R4-NH—(C=O)—Y—Z—SS; and (ii) recovering the product (IB).

When Y is selected to be absent or —CH$_2$—, and X is S, a product referred to as product (IC), is prepared by process (IC) which comprises the steps of:

(i) reacting a starting material of formula:

(C) R1-(C=X)—Y—Z—SS, wherein R1 is —OH, and X is O, (C)

with a reactant of formula:

R4-NH$_2$ (D)

to form the product (IB) of formula:

R4-NH—(C=O)—Y—Z—SS;

(iii) thionating the product (IB) to form the product (IC) of formula:

R4-NH—(C=S)—Y—Z—SS, provided that if Y is absent, Z does not comprise an immediately adjacent carbonyl; and (iv) recovering the product (IC).

Those skilled in the art will appreciate that a wide variety of thionating conditions may be employed in the thionating step of this procedure. For example, Lawesson's reagent (also referred to as "LR", which is a thionation reagent well known in the art), or P$_2$S$_5$ in mild base (e.g. pyridine or sodium bicarbonate), or like means, may be employed to achieve this result.

When Y is selected to be absent or —CH$_2$—, and X is NR7, a product referred to as product (ID), is prepared by process (ID) which comprises the steps of:

(i) reacting a starting material of formula:

R1-(C=X)—Y—Z—SS, wherein R1 is —OH, and X is O, and if Y is absent, Z does not comprise an immediately adjacent carbonyl, with a reactant of formula:

R4-NH$_2$ (D)

to form the product (IB) of formula:

R4-NH—(C=O)—Y—Z—SS;

(iii) thionating the product (IB) to form the product (IC) of formula:

R4-NH—(C=S)—Y—Z—SS;

(iv) reacting the product (IC) with an alkylating agent capable of contributing an alkyl group R11, which is preferably lower alkyl to form the intermediate (H) of formula:

R4—N=(C—S—R11)—Y—Z—SS; and (H)

(v) reacting the intermediate (H) with $NH_2$—R7, to form the product (ID) of formula:

R4—NH—(C=NR7)—Y—Z—SS;

(v) recovering the product (ID).

It will be appreciated that a wide variety of alkylating conditions may be employed to achieve the desired alkylation. For example, the alkylating agent may be selected from the group consisting of iodomethane, iodoethane, methylbromide, ethylbromide, allylbromide, allylchloride, dimethylsulfate, $CH_3OSO_2CF_3$, and the like.

While it will be appreciated that reagents are available wherein each synthetic route may be conducted with X being oxygen, sulfur or NR7, wherein reagent (B), for example, is selected to be a thiodiimidazole or thiophosgene, or an imine diimidazole. Thus, according to Synthetic Route 2, reactant (E) is prepared by a process wherein X of reactant (B) is a sulfur or wherein X is NR7. When X is an oxygen, the oxygen in the derivatized resin (I) R4-NH—(C=X)—Y—Z—SS produced by any of the Synthetic Routes disclosed herein may be converted to a sulfur or —NR7 by thionation, to derive X as a sulfur and optionally alkylating the sulfur followed by contacting with $NH_2$—R7, to produce the product wherein X is NR7. From the foregoing disclosure, it will also be appreciated by those skilled in the art that the product wherein X is NR7 may also conveniently be derived by directly reacting a starting material wherein X comprises NR7, which comprises the steps of:

(i) reacting a starting material of formula

OH—(C=NR7)—Y—Z—SS, (C)

with a reactant of formula:

R4-$NH_2$ (D)

to form the product (ID) of formula:

R4-NH—(C=NR7)—Y—Z—SS; and (ii) recovering the product (ID).

In carrying out this embodiment of the synthetic method, the starting material (C) wherein R1 is —OH, X is NR7, and Y is not absent, may be prepared, for example, by contacting a reactant of formula (B):

R1-(C=X)—R2, wherein X is NR7, and R1 is —OH, (B)

with a starting material of formula (G):

T—Z—SS, (G)

to form the starting material (C) wherein X is NR7, R1 is —OH, and the reaction of T with reactant (B) results in formation of the moiety Y.

For purposes of this aspect of the invention, the reagent (B) preferably is or is formed from a diimidazole imine, such as phosgeneimine diimidazole.

As will be appreciated from the foregoing disclosure, products (IE, IF, and IG) may also be prepared according to the following embodiments of Synthetic Route 4, comprising the steps of:

(i) reacting a starting material of formula (W):

HOOC—NH—Q—R8 (W)

with reactant (D) of formula

R4-$NH_2$ (D)

to form intermediate (J) of formula:

R4-NH—(C=O)—NH—Q—R8; (J)

(ii) removing R8 from intermediate (J) to form intermediate (K) of formula:

R4-NH—(C=O)—NH—Q; and (K)

(iii) reacting the intermediate (K) with material (G) of formula:

T—Z—SS to form the product (IB) of formula: (G)

R4-NH—(C=O)—NH—Z—SS, (IE)

wherein all variables are as previously defined.

Where X is S, prior to removal of R8, intermediate (J) is thionated to form intermediate (L) of formula:

R4-NH—(C=S)—NH—Q—R8, (L)

which is then deprotected and reacted with T—Z—SS to form product (IF).

Likewise, where X is desired to be NR7, prior to deprotection, intermediate (L) is contacted with an alkylating agent capable of contributing an alkyl group R11 to form the intermediate (M) of formula:

R4-N=(C—S—R11)—Q—R8; (M)

which is then reacted with (H) $NH_2$—R7, deprotected and reacted with T—Z—SS (G) to form product (IG).

It will be appreciated that a wide variety of alkylating agents may be used to achieve this purpose. Preferably, the alkylating agent is selected from the group consisting of iodomethane, iodoethane, methylbromide, ethylbromide, allylbromide, allylchloride, dimethylsulfate, and $CH_3OSO_2CF_3$.

As will be appreciated from the foregoing disclosure, the product (I) may be prepared by a number of specific variations of the general methods described above. By way of summary, it will be appreciated that depending on the desired properties of product (I), different starting materials, reactants, and intermediates, as set forth above, may be reacted in various synthetic combinations. It will further be appreciated that in general, where the group "C=X" is "C=O", it is preferred for Y, Z or any other immediately adjacent group to not be a carbonyl group.

It will also be appreciated that when R4 is —OH, or —O—R3, (in which event R4 is referred to herein as R4'), the final product is useful in the production of hydroxamic ester compounds, which may be reduced to form an aldehyde, or to conduct other desirable chemistry, including but not limited to esterifying the resin at the free amino hydroxyl group.

d. Further Description of Key Reactants Utilized According to Synthetic Routes 1–4:

i. Reactants (A) and (G), Derivatives thereof, and Solid Supports Useful According to the Methods of this Invention:

Those skilled in the art will know, based on the extensive disclosure provided herein, which solid supports may be used to advantage according to the present disclosure. By way of specific guidance, however, it is noted that solid supports having a formula (A) R—Y—Z—SS, including, for example, $NH_2$—SS are commonly known, are commercially available and may be readily prepared by those of ordinary skill in the fields of combinatorial chemical synthesis and peptide synthesis. For instance, a variety of $NH_2$—SS resins are commercially available from Novabiochem, Advanced Chemtech, Bachem, and Peptide International, as well as other commercial sources. Specific resins that may be derivatized according to the present invention include, but are not limited to water soluble polymers, cottons, sheets, glasses, fiberglasses, pins, polystyrene polymers and resins, each of which has at least one functional amine group. Especially preferred selections for $NH_2$—SS are resins, most especially aminomethylated polystyrene resin and 4-methyl benzhydrylamine resin, which are available from commercial sources, including those listed above.

Solid supports of formula (G) T—Z—SS, as used according to specific synthetic methods disclosed herein, include the $NH_2$—SS support discussed above, as well as those having functional chloride or carboxylic acid groups in place of the functional amine group. Such supports are available from the commercial sources noted above, as well as other commercial sources, and may be readily prepared according to methods known in the art.

Polymeric resins having one or more of the following characteristics are suitable for use as solid supports according to the method of this invention:

1. Resins which are insoluble in polar aprotic solvents such as dimethyl formamide (DMF), N-methylpyrrolidone, tetrahydrofuran (THF), and other solvents conventionally used in solid-phase peptide synthesis (such as dichloromethane or methanol).
2. Resins which are microporous and which have high surface areas in polar aprotic solvents.
3. Resins which are capable of being functionalized with groups which can react with aldehyde or ketoamide groups to form a bond which is stable during the subsequent addition of amino acids (or amino acid analogs) to the N-terminal end of the growing peptide chain.
4. Resins which are stable in the presence of reagents such as TFA, diisopropylethyl amine, dicyclohexylcarbodiimide (DCC) and other reagents conventionally used in solid phase peptide synthesis.

ii. Reactant (B), of Formula R1-(C=X)—R2:

Reactant (B) is employed according to various embodiments of this invention, as described above. With respect to R1 and R2 of reactant (B), R2 is chosen for its ease of departure upon reaction with the solid support amino functional groups, and R1 is chosen for its ease of departure upon reaction with the amino group of reactant (D). R1 and R2 can be the same or different. Suitable R1 substituents include but are not limited to those in the group consisting of imidazole, p-nitrophenoxy, Cl, succinimidyl, and Me-imidazolium. Suitable R2 substituents include those in the group consisting of imidazole, Cl, succinimidyl, and Me-imidazolium. Preferred combinations of R1 and R2 include those where R1 and R2 are the same, or where R1 is p-nitrophenoxy and R2 is Cl. A preferred X in reactant B is N-alkyl, oxygen, sulfur, with oxygen being most preferred. When X is oxygen, an especially preferred reactant (B) is selected from the group consisting of 1,1-carbonyldiimidazole, p-nitrophenyl-chloroformate, phosgene, N,N'-disuccinimidyl carbonate, and 1,1-carbonyldimethyldiimidazolium. When X is NR7, a preferred reactant (B) is a diimidazole imine, such as phosgeneimine diimidazole. When X is sulfur, a preferred reactant (B) is 1,1'-thiocarbonyldiimidazole or thiophosgene. Reactant (B) of formula R1-(C=S)—R2 is chosen when functionalities in the final product other than carbonyl are desired Accordingly, choice of this reactant permits the production of a product bearing the group —C=NR7, wherein R7 is a hydrogen or is an alkyl, alkenyl, aryl, aralkyl, cycloalkyl or heterocyclic substituent.

iii. Reactant (D) of Formula R4-$NH_2$:

As defined above, R4 may be —OH, —$NH_2$, —O—R3, or —NH—R3, wherein R3 is a protecting group. Suitable protecting groups are described below and are known in the art and can be found, for example, in "Protective Groups in Organic Synthesis", T. Greene, (John Wiley & Sons, Inc., 1991). When R4 is R3-NH—, preferred R3 protecting groups include Cbz, Boc, Alloc, Fmoc, Troc, Me3Si($CH_2$)$_2$OCO, and PMC. Preferred species of reactant (D) include $NH_2$—$NH_2$ and R3-NH—$NH_2$, wherein R3 is selected from the group consisting of Cbz, Boc, Alloc, Fmoc, Troc, and $Me_3Si(CH_2)_2OCO$.

iv. Protecting Groups:

It will be appreciated, particularly in the synthesis of peptides, peptide analogs and peptidomimetic compounds, that where reactive moieties are present, as in reactive amino acid side chains, if reactions at that reactive moiety is not desired, methods are known for protecting such sites. Accordingly, where a reactive heteroatom exists in an amino acid side chain, or where reaction at an amino acid or amino acid analog's amino-terminal nitrogen is to be avoided, the following guidelines and procedures will apply. However, where side chains are non-reactive, those skilled in the art will appreciate that protection is not required (e.g. methylcysteine is already effectively protected; the phenylalanine side chain is relatively non-reactive). In particular, with regard to an argininal moiety, wherein the side chain has a guanidino group (the arginine side chain is: —$(CH_2)_3$—NH—(C=$NH_2^+$)—$NH_2$, wherein the moiety —NH—(C=$NH_2^+$)—$NH_2$ represents the guanidino functionality), single or double protection of the side chain may be desirable or essential in order to achieve a desired reaction at another side, e.g., at the amino-terminal nitrogen, without production of a plurality of unwanted side-chain reactions. It will also be appreciated that while the argininal moiety exists in solution in various tautomeric forms, appropriate side-chain protection may be employed to keep the side chain in a linear form.

In practicing the methods of the present invention, the following considerations apply to the selection of α-amino protecting groups, side chain protecting groups, and carboxy protecting groups, all of which are preferably used to protect sites on a peptide chain synthesized using the present derivatized resin. In selecting suitable α-amino protecting groups (PG1) to be used during the synthesis of desirable peptidyl or peptidomimetic compounds using the resins of this invention, the α-amino protecting group should:

(i) render the α-amino function inert under the conditions employed in the coupling reaction;
(ii) be readily removable after the coupling reaction under conditions that will not remove side chain or carboxy terminus protecting groups; and
(iii) eliminate the possibility of racemization upon activation prior to coupling.

A suitable α-amino protecting group may be selected from the group consisting of acid labile α-amino protecting groups (cleavage conditions are noted in brackets [ ]):

(a) Triphenylmethyl (trityl) group is cleaved under very mild acid conditions [1% TFA].
(b) tert-Butyloxy carbonyl (Boc), t-amyloxycarbonyl, adamantyloxycarbonyl, 4-methoxy benzyloxycarbonyl; these protecting groups require moderately strong acids such as trifluoroacetic acid, hydrochloric, or boron trifluoride in acetic acid for their removal.

(c) Benzyloxycarbonyl (CBz), 2-chlorobenzyloxycarbonyl (2-ClZ), cycloalkyloxycarbonyl, and isopropyloxycarbonyl, require stronger acids, such as hydrogen fluoride, hydrogen bromide or boron trifluoroacetate in trifluoro acetic acid for their removal. The CBz and the 2-ClZ groups may also be cleaved by hydrogenation under palladium on carbon in methanol. A suitable α-amino protecting group also may be selected from the group consisting of base labile α-amino protecting groups. For instance, Fluorenylmethyloxycarbonyl (Fmoc) may be cleaved by using 20% piperidine/DMF or excess diethylamine in THF. Allyloxycarbonyl (Alloc) may be cleaved by Pd (0) catalyst transfer of the allyl group to a nucleophile such as morpholine, dimedone, tributyl tin hydride and N-methyl aniline. Preferred α-amino protecting groups (PG) include Boc, Fmoc, Alloc, and Cbz.

An amino acid side-chain protecting group should:
(i) render the protected side chain functional group inert under the conditions employed in the coupling reaction;
(ii) be stable under the conditions employed in removing the α-amino or the carboxy terminus protecting groups, and
(iii) be readily removable upon completion of the desired peptide under reaction conditions that will not alter the structure of the peptide chain. A suitable amino acid side chain protecting group may be selected from the group consisting of (methods for cleavage of these protecting groups are shown in brackets [ ]):

(a) for protection of lysine amino groups, any of the groups mentioned above for the protection of α-amino protecting groups are suitable.

(b) for protection of arginine guanidino group, the preferred protecting groups include nitro [H2/Pd/C, HF], benzyloxycarbonyl (CBz) [HF, TFMSA, TMSOTf, H2/Pd/C], tert-butyloxycarbonyl (Boc) [TFA], 2,2,5,7,8-pentamethylchroman-6-sulfonyl (Pmc) [TFA], 2,3,6-trimethyl-4-methoxyphenylsulfonyl (Mtr) [TFA], p-toluenesulfonyl (Tos) [HF, TFMSA], mesitylene-2-sulphonyl (Mts) [HF, TFMSA], allyloxycarbonyl (Alloc) [Pd(0), morpholine or dimedone].

(c) For protection of serine and threonine hydroxyl groups, protecting groups include trityl [1% TFA], tert-butyl [TFA], benzyl, and substituted benzyl groups such as 4-methoxybenzyl, 4-chlorobenzyl, 2-chlorobenzyl, and 2,6-dichlorobenzyl which are cleaved by a similar method [HF, TFMSA, H2/Pd/C].

(d) For protection of tyrosine phenolic group, protecting groups such as tert-butyl [TFA], trityl [1% TFA], benzyl, 2-bromobenzyl and 2,6-dichlorobenzyl, all cleaved by the same reagents [HF, TFMSA, H2/Pd/C], are suitably employed.

(e) For protection of aspartic and glutamic acid side chain carboxy group, protecting groups include methyl [OH-, H+], ethyl [OH-, H+], t-butyl [TFA], allyl [Pd(0), morpholine], cyclohexyl [HF, TMSOTf], or benzyl groups [HF, TFMSA, TMSOTf, H2/Pd/C].

(f) For protection of asparagine and glutamine side chain, protecting groups include trityl [TFA] and xanthyl [TFA].

(g) For protection of histidine imidazole group, suitable protecting groups include 2,4-dinitrophenyl (Dnp) [thiophenol], trityl [TFA], benzyloxymethyl (Bom) [HF, TFMSA, TMSOTf, H2/Pd/C], p-toluene sulfonyl (Tos) [HF, TFMSA], and benzyloxycarbonyl (Cbz) [HF, H2/Pd/C].

(h) For protection of cysteine sulfhydryl group, suitable protecting groups include trityl [TFA], 4-methylbenzyl (pMeBzl) [HF, TFMSA], 4-methoxybenzyl (pMeOBzl) [HF, TFMSA], acetamidomethyl (Acm) [I2, Hg2+], tert-Butyl (tBu) [Hg2+].

(i) For protection of tryptophan indole group, suitable protecting groups include formyl [10% piperidine in DMF, followed by HF] and tert-butyloxycarbonyl (Boc) [TFA].

A carboxy terminus protecting group (PG2) should:
(i) render the protected functional group inert under the conditions employed in the coupling reaction,
(ii) be stable under the conditions employed in removing the α-amino or the side chain protecting groups, and
(iii) be readily removable upon completion of the desired peptide under reaction conditions that will not alter the structure of the peptide chain. For the protection of the carboxy terminus of amino acids suitable protecting groups include methyl [OH—, H+], ethyl [OH-, H+], tert-butyl [TFA], benzyl [OH-, H2/Pd/C] and allyl [Pd(0), morpholine] groups.

e. Preferred Aspects of the Invented Methods for Production of the Resin (I):

A preferred embodiment of the method of this invention comprises selection of aminomethylated polystyrene resin or 4-methyl benzhydrylamine resin as $NH_2$—SS, reactant (A) wherein Z is absent, selection of reactant (B) from the group consisting of 1,1-carbonyldiimidazole, p-nitrophenylchloroformate, phosgene, N,N'-disuccinimidyl carbonate, and 1,1-carbonyldimethyldiimidazolium, and selection of —NH—R3 as R4 in reactant (D), with R3 selected from the group consisting of Cbz, Boc, Alloc, Fmoc, Troc, $Me_3Si(CH_2)_2OCO$, and PMC. Aminomethylated polystyrene resin is most preferred.

Where utilized, a resin of formula (G) T—Z—SS preferably comprises a functional amine group. Selection of T—Z—SS to be aminomethylated polystyrene resin or 4-methyl benzhydrylamine resin is especially preferred.

Where X in reactant (B) is sulfur, the selection of 1,1'-thiocarbonyl-diimidazole or thiophosgene as reactant (B), and the selection of $NH_2$ or P3-NH— as the R4 group in reactant (D) is preferred for preparation of a solid support of formula R4-NH—(C=S)—NH—SS. When R4 is selected to be R3-NH—, preferably, the R3 protecting group is removed from the solid support thus formed to yield an —$NH_2$ terminal substituent on the solid support.

In a preferred embodiment, the product (I) is selected to have a formula $NH_2$—NH—(C=O)—NH—SS, as disclosed in Examples 1, 2, and 3, and elsewhere throughout the specification. Reaction of an aldehyde or ketoamide with the —$NH_2$ moiety of the resin results in immobilization of the aldehyde or ketoamide. Subsequent chemical modification thereof, as in peptide synthesis, combinatorial chemistry and the like, results in production of a reaction product immobilized on the resin through a semicarbazone moiety. Release of the immobilized aldehyde or ketoamide, or a derivative thereof which is subjected to chemical modification while being immobilized on the resin, is thereafter achieved as disclosed herein, in view of which methods known in the art for cleavage of the semicarbazone moiety may be employed.

In view of the foregoing disclosure, it will be apparent that this invention contemplates methods of preparing a derivatized solid support having a formula including, but not limited to those represented by any of the following, with all variables as defined above:

| | |
|---|---|
| R4—NH—(C=X)—Y—Z—SS | (I) |
| R4—NH—(C=X)—NH—Z—SS | (IA) |
| R4—NH—(C=X)—NH—SS | (IA) |
| R4—NH—(C=O)—NH—Z—SS | (IB) |
| R4—NH—(C=O)—CH$_2$—Z—SS | (IB) |
| R4—NH—(C=O)—Z—SS | (IB) |
| R4—NH—(C=O)—SS | (IB) |
| R4—NH—(C=S)—NH—Z—SS | (IC) |
| R4—NH—(C=S)—CH$_2$—Z—SS | (IC) |
| R4—NH—(C=S)—Z—SS | (IC) |
| R4—NH—(C=S)—SS | (IC) |
| R4—NH=(C—NR7)—NH—Z—SS | (ID) |
| R4—NH=(C—NR7)—CH$_2$—Z—SS | (ID) |
| R4—NH=(C—NR7)—Z—SS | (ID) |
| R4—NH=(C—NR7)—SS | (ID) | wherein SS is a solid support, and all other variables are as previously defined. The invented solid supports prepared according to the synthetic methods disclosed herein may be stored dry in a dessicator, preferably under refrigeration or at room temperature. Resins prepared according to the invented methods are stable under these conditions for six months or longer.

B. Reacting an Aldehyde or ketoamide with the Derivatized Resin of Step (A), thereby Producing an Immobilized Aldehyde or Ketoamide:

Upon production, according to the above described method of this invention, of a suitably derivatized resin of formula (I)

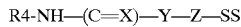

R4-NH—(C=X)—Y—Z—SS an appropriately protected aldehyde or ketoamide is reacted with the derivatized resin (I), produced as described above in step (A). As such, the resin may be viewed as a protecting group of the aldehyde or ketoamide moiety. The resin may also conveniently be viewed as a tether or means for immobilization of the aldehyde or ketoamide. Desirably, the aldehyde or ketoamide is reacted with the derivatized resin so as to produce a product which may be later cleaved from the resin to produce a desired peptide or peptidomimetic product, such as, for example, a pharmacologically significant protease inhibitor being a terminal aldehyde or ketoamide moiety.

Upon production of the resin (I), wherein R4 is —NH—R3, the protecting group R3 is removed to yield a free amino group. Contacting an appropriately protected aldehyde or ketoamide with the free amino group, as described herein and as specifically exemplified hereinbelow, results in the formation of a semicarbazone moiety. In one preferred embodiment of the invention, the aldehyde is an appropriately protected argininal or an argininal peptide. Where an agininal is reacted with the resin, (i.e. the P1 position of a larger molecule is intended to be an argininal), and where further chemistry is to be conducted (e.g. peptide synthesis on the amino terminus of the argininal), it is preferred for the argininal to be orthogonally protected. In one preferred example of such orthogonal protection, it is preferred for the argininal side-chain amino groups to be di-Alloc or di-Boc protected, and the argininal amino terminal nitrogen to be Fmoc protected. In this manner, Fmoc peptide synthesis may be safely conducted, without the danger of deprotection of the argininal side-chain amino groups in the course of subsequent peptide synthesis steps at the argininal amino terminus. Furthermore, upon completion of the peptide synthetic steps, the peptide may conveniently be cleaved from the resin and the di-Boc or di-Alloc protection may be removed, in a single step, and under relatively mild acid- cleavage conditions, preferably including treatment with TFA; TFA:H$_2$O, 9:1; TFA:DCM: H$_2$O, 8:1:1; as opposed to HF treatment, relatively rapidly and with reduced danger of aldehyde dehydration to undesirable covalent adducts. Those skilled in the art will appreciate, based on this disclosure, that it is preferred for the lowest acid concentration and the shortest time to be used consistent with efficient cleavage and deprotection.

Those skilled in the art will appreciate that while the orthogonal protection described herein is preferred, under certain synthetic conditions, for example where harsh acidic conditions are required for synthetic steps subsequent to coupling of the aldehyde to the resin, the di-Boc or di-Alloc combined with Fmoc synthetic chemistry may result in premature deprotection of the argininal side chain amino groups. Accordingly, other known synthetic regimens would need to be employed under those circumstances.

It will also be appreciated from the foregoing disclosure that aldehyde or ketoamide isolation or purification may be achieved by contact with the derivatized resin produced according to the method of this invention, and subsequent cleavage and recovery from the resin of the free aldehyde or ketoamide.

C. Optionally Performing Solid-phase Chemistry on the Immobilized Aldehyde or Ketoamide of Step (B), Selected from Peptide Synthesis, Synthesis of Peptide Analogs, and Combinatorial Chemistry:

Once immobilized on the resin, solid-phase synthetic manipulation of aldehydes and ketoamides may be conducted. Standard solid-phase peptide synthetic methods may be employed, bearing in mind the specifics of the disclosure and preferences described herein. Thus, for example, it is preferred where a di-Boc argininal is desired to be directly coupled to the resin, Fmoc protection of the argininal amino-terminal nitrogen is employed. In this way, N-terminal chemistry may be conducted, without disrupting the side-chain protection.

According to the method disclosed herein, any of a wide variety of pharmacologically significant peptide or peptidomimetic compounds may be produced. Of particular significance is the ability to efficiently synthesize peptide aldehydes and ketoamides for use as protease inhibitors, including inhibitors of proteases significant to the blood coagulation pathway, including but no limited to thrombin inhibitors, factor Xa inhibitors and the like. Specific compositions prepared and disclosed according to this aspect of the present invention include, but are not limited to:

t-Butoxycarbonyl-Hydrazyl-Carbonyl-Amino Methylated polystyrene resin;

Hydrazyl-Carbonyl-Amino Methylated polystyrene resin;

N$^\alpha$-Boc-N$^\delta$-(di-Alloc)Arginal-hydrazylcarbonyl-amino methylated polystyrene resin;

N$^\delta$-(di-Alloc)-Argininal-hydrazylcarbonyl-amino methylated polystyrene resin;

Benzylsulfonamido-6Lactam-Gly-N$^\delta$-(di-Alloc)-Argininal-hydrazylcarbonyl-amino methylated polystyrene resin;

Benzylsulfonamido-6Lactam-Gly-Argininal-hydrazylcarbonyl-amino methylated polystyrene resin;

N$^\alpha$-Boc-Gly(Allyl)al-HydrazylCarbonyl-Amino Methylated polystyrene resin;

N$^\alpha$-Gly(Allyl)al-HydrazylCarbonyl-Amino Methylated polystyrene resin;

hydrazonylcarbonyl aminomethylated polystyrene resin;

omega, omega'-di-N-t-butoxycarbonyl-Argininal hydrazonylcarbonyl aminomethylated polystyrene resin;

N-α-Fmoc-azeidine-2-carbonyl-omega, omega'-di-N-t-butoxycarbonyl-argininal hydrazonylcarbonyl aminomethylated polystyrene resin;

hydrazonylcarbonyl aminomethylated polystyrene resin;

N-α-Fmoc-seryl(O-t-Bu)-azetidine-2-carbonyl-N-omega, omega'-di-N-t-butoxycarbonyl-argininal hydrazonylcarbonyl aminomethylated polystyrene resin;

Seryl(O-t-Bu)azetidine-2-carbonyl-omega, omega'-di-N-t-butoxycarbonyl-argininal hydrazonylcarbonyl aminomethylated polystyrene resin;

N-α-benzenesulfonyl-D-seryl(O-t-Bu)-azetidine-2-carbonyl-omega, omega'-di-N-t-butoxycarbonyl-argininal hydrazonylcarbonyl aminomethylated polystyrene resin;

Nα-Fmoc-$N^d$-(di-Alloc)-Arginal-hydrazylcarbonyl-amino methylated polystyrene resin;

Those skilled in the art will appreciate from the foregoing disclosure that the derivatized resins according to the present invention may be utilized in any of a number of useful ways. Included among the methods of using the present resins are methods for solid-phase synthesis of peptides, methods for conducting combinatorial chemistry and methods for purifying or isolating proteins or peptides. Those skilled in the art will appreciate that other methods for using the derivatized resins according to the instant invention exist, and those methods likewise come within the scope of the present invention. Thus, for example, the resins according to the present invention are particularly useful in the solid-phase synthesis of protease inhibitors, and in particular inhibitors of serine proteases, such as thrombin and Factor Xa, urokinase, the NS3 protease of Hepatitis C virus and trypsin. Further specifics of these aspects of the method of this invention for utilization of the derivatized resin (I) are provided in further detail below:

i. Solid-phase Peptide Synthesis:

One aspect of the present invention includes the use of the synthetic method of this invention, including the generic and specific synthetic methods disclosed herein, and compositions made thereby, (collectively referred to as "the invented solid supports"), in the solid phase synthesis of peptide or peptidomimetic compositions. Preferred uses include use for the synthesis of peptide or peptidyl aldehydes or ketoamides, such as those that inhibit one or more serine proteases. An especially preferred use of the invented solid supports is use for the synthesis of inhibitors of thrombin, Factor Xa, urokinase, Hepatitis C enzymes, chymase, prostate specific antigen (PSA), Factor VIIa, elastase, and trypsin.

Examples 4–8 describe the use of synthetic methods disclosed herein to make a thrombin inhibitor. Examples 9–14 and 23–26 describe the use of the synthetic methods disclosed herein to make specific inhibitors of urokinase.

In a particularly preferred embodiment of this aspect of the invention, Boc protection of the aldehyde permits simultaneous deprotection of the peptide and cleavage of the peptide from the resin, to release the free aldehyde product.

According to this method of producing derivatized resins and use thereof to produce peptides of pharmacologic significance, R4 of the product (I), wherein R4 is R3-NH— is further derivatized such that a product is produced that may be represented by the formula (II):

PG—NH—C(R*)—CH=N—NH—(C=X)—Y—Z—SS,  (II)

wherein (R*) represents an amino acid side chain. Where an oligomer is produced according to this method, the product (I) is further derivatized at the R4 group to produce a product which may be represented by the formula (III):

(res)$_t$—NH—C(R*)—CH=N—NH—(C=X)—Y—Z—SS  (III)

wherein (res)$_t$ represents a peptide chain of "t" residues, wherein "t" is an integer between about 2 and about 50, and more preferably between about 3 and 10.

As a result of practicing the method of this invention, therefore, it will be appreciated that a product, including but not limited to the following variations on the derivatized resin represented by formula (III), is produced:

(res)$_t$-NH—C(R*)—CH=N—NH—(C=X)—Y—Z—SS;

(res)$_t$-NH—C(R*)—CH=N—NH—(C=X)—NH—Z—SS;

(res)$_t$-NH—C(R*)—CH=N—NH—(C=X)—NH—SS;

(res)$_t$-NH—C(R*)—CH=N—NH—(C=O)—NH—Z—SS;

(res)$_t$-NH—C(R*)—CH=N—NH—(C=O)—CH$_2$—Z—SS;

(res)$_t$-NH—C(R*)—CH=N—NH—(C=O)—Z—SS;

(res)$_t$-NH—C(R*)—CH=N—NH—(C=O)—SS;

(res)$_t$-NH—C(R*)—CH=N—NH—(C=S)—NH—Z—SS;

(res)$_t$-NH—C(R*)—CH=N—NH—(C=S)—CH$_2$—Z—SS;

(res)$_t$-NH—C(R*)—CH=N—NH—(C=S)—Z—SS;

(res)$_t$-NH—C(R*)—CH=N—NH—(C=S)—SS;

(res)$_t$-NH—C(R*)—CH=N—NH—(C=NR7)-NH—Z—SS;

(res)$_t$-NH—C(R*)—CH=N—NH—(C=NR7)-CH$_2$—Z—SS;

(res)$_t$-NH—C(R*)—CH=N—NH—(C=NR7)-Z—SS; and (res)$_t$-NH—C(R*)—CH=N—NH—(C=NR7)-SS.

It will further be appreciated from the foregoing disclosure that the group (res)$_t$, may be produced by standard solid-phase synthetic procedures known in the art wherein individual amino acid or amino acid analog residues are linked, one by one, to form the peptide or peptide analog. At each step, standard protection, deprotection, coupling and wash steps are conducted. In an alternate embodiment of this aspect of the invented method, blocks of separately synthesized residues, i.e. oligomers or polymers, may be contacted with the product represented by formula (II), to produce a product of formula (III), in a reduced number of steps. Equivalents and other variations suggested to those skilled in the art based on the foregoing disclosure may likewise be conducted without departing from the invention disclosed and claimed herein.

Cleavage of the peptide from the resin and deprotection results in production of the desired peptide or peptidomimetic product produced by extension of the peptide chain on the derivatized solid support according to the method of this invention.

ii. Combinatorial Chemistry:

The derivatized resin (I) produced according to the method of this invention is also useful in the field of combinatorial chemistry and development of chemical libraries. With reference to the following disclosure, it will be appreciated that preferred methods within this aspect of the invention result in the development of combinatorial libraries having an aldehyde or ketoamide in the P1 position, especially argininals and glycinals:

P$_4$—P$_3$—P$_2$—P$_1$

Those skilled in the art will recognize that while a molecule bearing four residues is represented, peptides or peptide analogs of any desired length may be prepared according to this method by repeating the coupling steps as many times as necessary. According to one embodiment of this aspect of the invention, a library is designed wherein the $P_1$ residue may be varied or kept constant while residues $P_4$, $P_3$, and $P_2$ are varied and incorporated into, for example, peptides and peptidomimetic $P_1$ aldehydes. Using the invented supports, multiple reactions are carried out in parallel. The $P_1$ site is first incorporated onto the resin, e.g. the HCAM resin of this invention, following procedures exemplified in Examples 1–5, followed by incorporation of variations in the $P_4$, $P_3$, and $P_2$ residues, thereby forming a library of peptide or peptidomimetic compounds available for structure-activity analyses in any of a number of in vitro or in vivo assay systems, including protease inhibition assays.

As will be appreciated by those skilled in the art, this process of library formation and parallel synthesis may be carried out in a number of known formats. In one embodiment, the synthesis is conducted in Whatman mini columns, or the like, wherein standard peptide synthetic methods known in the art are used to extend the peptide chain, with each subsequent coupling being achieved at the carboxy terminus of each added residue which is linked to the amino terminus of the previously immobilized residues.

Following synthesis, the multiple peptide variants are cleaved from the resin, isolated, and tested for biological activity. Likewise, with the aid of the invented solid supports, automated synthesis of a library of peptides or peptide analogs may be conducted in commercially available peptide synthesizers.

Thus, this aspect of the invention represents a method for making a library of peptides or peptide analogs comprising the steps of:

(a) in each of a series of separate containers or reaction vessels, contacting an aldehyde or ketoamide with a derivatized resin represented by formula (I) under conditions which permit the formation of a stable semicarbazone, thereby immobilizing said aldehyde or ketoamide to produce a $P_1$ residue;

(b) in each of said series of separate containers or reaction vessels, contacting same or different amino acid residues or amino acid analog residues with the thus immobilized aldehyde or ketoamide under conditions permitting formation of a peptide bond so as to produce a series of $P_2$ residues, same or different, in each of said series of separate containers or reaction vessels; and (c) repeating step (b) as many times as required so as to produce a sequential series of P residues to generate a peptide or peptide analog of the desired number of residues, with appropriate intermediate steps of protection and deprotection of reactive groups present on the growing peptide or peptide analog chain.

Standard peptide synthetic methods may be employed in this process, subsequent to the initial formation of the aldehyde-resin or ketoamide-resin linkage, as described above. Subsequent to cleavage from the resin, the thus synthesized library of peptides or peptide analogs bearing the original aldehyde or ketoamide as the $P_1$ residue may then be purified and tested for biological activity.

iii. Peptide or Protein Purification and Separation:

A further use of the invented solid supports, which comprise an amine, is in the field of purification and separation. The solid supports can be used to bind to, and thereby immobilize and isolate from solution, any composition bearing a reactive carbonyl component. The solid support-bound, carbonyl containing component may be a contaminant, as thus removed to increase purity of the starting solution, or it may be a desired product, in which case binding serves as step in the purification of the product.

For instance, the invention contemplates a method of isolating an aldehyde- or ketoamide-containing compound or composition from a solution, comprising the steps of:

(a) contacting a solution comprising an aldehyde or ketoamide with derivatized resin represented by formula (I) under conditions permitting interaction of the aldehyde carbonyl with the amine of the derivatized resin; and (b) allowing sufficient time for the interaction to proceed to completion such that the aldehyde or ketoamide is bound to the derivatized resin, thereby removing the aldehyde- or ketoamide-containing compound from the solution.

Optionally, the aldehyde or ketoamide can be removed from the derivatized resin by hydrolysis using procedures like those set forth in the specific exemplary support presented herein, and recovered by filtration in Whatman mini-columns or the like.

D. Cleaving, Deprotecting and Recovering the Product of Step (C) as the Free Aldehyde or Ketoamide.

Based on the foregoing disclosure, those skilled in the art will appreciate that production of pharmacologically significant peptide or peptide analog products bearing an aldehyde or ketoamide in the P1 position is enabled by this disclosure. Upon completion of the peptide synthetic steps, the peptide may conveniently be cleaved from the resin. Where di-Boc or di-Alloc protection has been employed, as described above, the protecting groups may be removed and the peptide cleaved from the resin, in a single step, and under relatively mild acid-cleavage conditions (e.g. TFA; TFA:$H_2O$, 9:1; TFA:DCM: $H_2O$, 8:1:1; as opposed to HF treatment), relatively rapidly and with reduced danger of aldehyde dehydration to undesirable covalent adducts. Those skilled in the art will appreciate, based on this disclosure, that it is preferred for the lowest acid concentration and the shortest time to be used, consistent with efficient cleavage and deprotection. Depending on the type of protection, higher acid concentrations and cleavage/deprotection times may be required. Bearing this disclosure and specific guidance in mind, those skilled in the art are well aware of methods for peptide cleavage, deprotection and product recovery, which in this case permits facile recovery of product bearing a P1 aldehyde or ketoamide moiety.

SPECIFIC EXEMPLARY SUPPORT

Having generally described the invention with respect to the preferred embodiments thereof, the following specific exemplary disclosure is provided. The specifics of these examples are provided to supplement the written description of this invention. However, the specifics of these examples should not be construed as limiting on the invention.

EXAMPLE 1

Preparation of t-Butoxycarbonyl-Hydrazyl-Carbonyl-Amino Methylated polystyrene resin

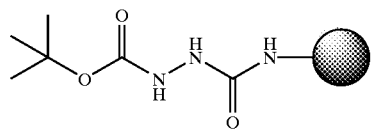

To a suspension of 1,1-carbonyldiimidazole (29.19 g, 180 mmol, 6 equiv.) in dimethylformamide (300 mL) was added portionwise t-butylcarbazate (23.76 g, 180 mmol, 6 equiv.) with stirring at ambient temperature under a nitrogen atmosphere. After the addition was completed, the reaction was allowed to stir at room temperature for 2½ hours and then poured into amino methylated polystyrene resin (30 g, 30 mmol, 1 meq/g, Advanced Chemtech) in the peptide synthesis flask. The suspension was purged with nitrogen gas for 3 hours. The resin was filtered and washed with 3×350 mL portions of methylene chloride. Kaiser Test (solution and bead; light blue, clear). A double coupling was undertaken to ensure a quantitative reaction, although double coupling is optional. Thus, a solution of 1,1-carbonyldiimidazole (14.60 g, 90 mmol, 3 equiv.) and t-butylcarbazate (11.88 g, 90 mmol, 3 equiv.) in 150 dimethylformamide was stirred at ambient temperature for 30 minutes and then poured into the previously prepared resin. After purging with nitrogen gas for 1 hour, the resin was filtered and washed with 6×350 mL portions each of methylene chloride, methanol, methylene chloride, methanol, methylene chloride, and methanol. Kaiser Test (solution and bead; clear and clear). Subsequent coupling reactions were carried out when necessary. The resin was dried under vacuum and acetylated with DMP/ acetic anhydride/$Et_3N$ (8:1:1; about 300 ml.) for 30 minutes at ambient temperature. The resin was successively washed three times each with solvents (methylene chloride and methane) and dried under vacuum to afford product in quantitative yield.

EXAMPLE 2

Hydrazyl-Carbonyl-Amino Methylated polystyrene

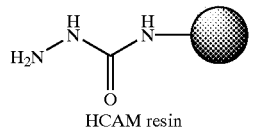

HCAM resin

A solution of DCM/TFA (1:1) (300 mL) and thioanisole (10 mL) was added to the resin of Example 1 (30 g) to effect deprotection. The mixture purged slowly with nitrogen gas in the peptide synthesizer flask at ambient temperature for 30 minutes. The deprotected resin was filtered and washed with DCM (2×), DCM/DIEA (2×), DCM (2×), and alternatively with organic solvents (methylene chloride, methanol). The resulting title resin was dried under vacuum. Kaiser Test (solution and bead; light blue, sand color); Overall yield: 30.64 g resin (approx. 0.85 mmol/g or 0.85 meq semicarbazide/g).

EXAMPLE 3

Preparation of Hydrazyl-Carbonyl-Amino Methylated polystyrene resin

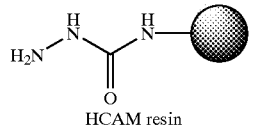

HCAM resin

To amino methylated polystyrene resin (1.0 g, 1.0 mmol, Advanced Chemtech) in N,N-dimethylformamide (12 mL) was added 1,1-carbonyldiimidazole (3.89 g, 24.0 mmol, 24 equiv.). The suspension was shaken at room temperature for 5 hours and then filtered in a peptide synthesis flask. The resin was washed with copious amounts of methylene chloride. Kaiser Test (solution and bead; light blue, white). A 2M solution of hydrazine in N,N-dimethylformamide (12 mL) was added to the resin and allowed to shake at ambient temperature overnight. The resin was filtered and washed alternately with organic solvents (methylene chloride and methanol) and dried under vacuum to afford product 1.06 g (approx. 0.94 mmol/g).

EXAMPLE 4

Preparation of $N^\alpha$-Boc-$N^\delta$-(di-Alloc)-Argininal-hydrazylcarbonyl-amino methylated polystyrene resin

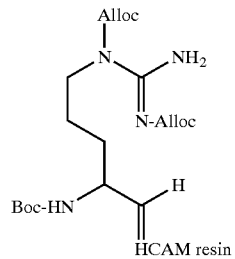

t-butoxycarbonyl-L-Arg(alloc)$_2$-al (129 mg, 0.30 mmol, 2 equiv.; see Examples 15 and 16 for synthesis) was added to a suspension HCAM resin of Example 2 or 3 (200 mg, 0.15 mmol) in methylene chloride (2.52 mL) in a Whatman mini-column tube. The mixture was allowed to shake for 24 hours at ambient temperature. The resin was filtered and washed with copious amounts of solvents (methylene chloride, methanol, and ether). Kaiser Test (solution and bead; clear and clear). The resin was dried under vacuum to afford 213 mg resin (approx. 0.57 mmol/g).

EXAMPLE 5

Preparation of $N^{67}$-(di-Alloc)-Argininal-hydrazylcarbonyl-amino methylated polystyrene resin

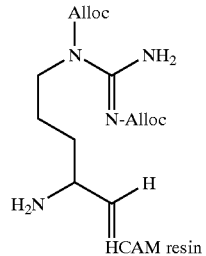

A solution of DCM/TFA/Thioanisole (7:3:1) (5 mL) was added to the resin of Example 4 (210 mg, 0.12 mmol). The mixture was allowed to shake in a Whatman mini-column tube at ambient temperature for 15 minutes. The deprotected resin was filtered and washed with DCM (3×), DCM/DIEA (2×), DCM (2×), MeOH (2×), DCM (3×). The resulting title resin was dried under vacuum. Kaiser Test (solution and bead; blue and light brown); Resin substitution (0.61 mmol/ g).

EXAMPLE 6

Preparation of Benzylsulfonamido-6Lactam-Gly-N$^\delta$-(di-Alloc)-Argininal-hydrazylcarbonyl-amino methylated polystyrene resin

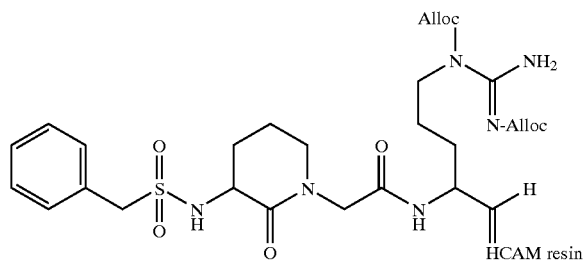

To a suspension of the resin of Example 5 (70 mg, 0.04 mmol), N-benzylsulfonyl-norVal(cyclo)-Gly-OH (19.6 mg, 0.06 mmol, 1.4 equiv.; see Example 11 of U.S. Pat. No. 5,703,208 for synthesis) and PyBOP (31.3 mg; 0.06 mmol, 1.4 equiv.) in DMF (0.8 mL), was added DIEA (7.8 mg, 0.06 mmol, 1.4 equiv.). The mixture was allowed to shake in a Whatman mini-column at ambient temperature overnight. The resin was filtered and washed with organic solvents (methylene chloride and methanol) and dried. Kaiser Test (solution and bead; clear and clear). Based on theoretical yield (83 mg), Resin substitution (0.51 mmol/g).

EXAMPLE 7

Preparation of Benzylsulfonamido-6Lactam-Gly-Argininal-hydrazylcarbonyl-amino methylated polystyrene resin

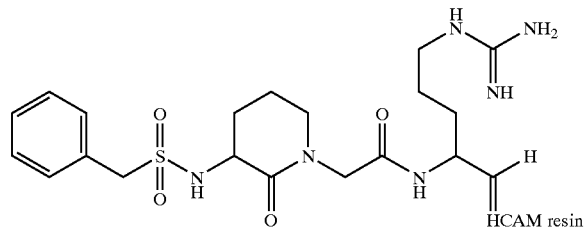

To a solution of THF/DMSO/0.5N HCl/Morpholine (2:2:1:5) (1.5 mL) was added the resin of Example 6 (83 mg, 0.043 mmol) and (Ph3P)4 Pd (33 mg, 0.65 equiv.). The mixture was allowed to shake in a Whatman mini-column at room temperature for 4 hours. The resin was filtered and washed with organic solvents (methylene chloride and methanol) and dried. Based on theoretical yield (76 mg), Resin substitution was estimated to be (0.56 mmol/g).

EXAMPLE 8

Preparation of Benzylsulfonamido-6Lactam-Gly-Argininal

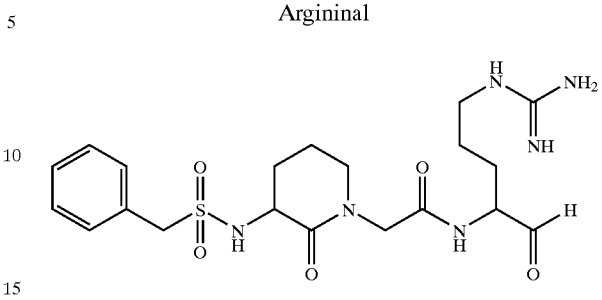

A solution of TFA/H$_2$O (8:2) (1.5 mL) was added to the resin of Example 7 (75 mg, 0.039 mmol) in a Whatman mini-column. The mixture was allowed to shake by mechanical shaker for 1⅓ hours at ambient temperature. The filtrate was purified with a Sepak column, using a H$_2$O, 0.1% acetonitrile; 10, 0 to 5, 5 gradient to afford 9.1 mg (50.0% yield) of title product as a white-powder (fluffy).

MS (M+H)=467.0, calculated (MW)=465.6.

HPLC retention, 10.9, 11.8, and 13.0 min. (2 cyclol and hydrate forms of the argininal derivative); C18 5–50% MeCN over 25 minutes, 1.0 mL/min.

The title compound was shown to have thrombin inhibitory activity in in vitro assays.

EXAMPLE 9

Preparation of N$^\alpha$-Boc-Gly(Allyl)al-HydrazylCarbonyl-Amino Methylated polystyrene resin

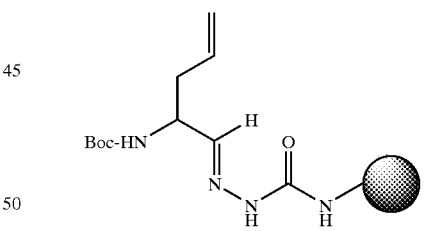

N$^\alpha$-Boc-Gly(Allyl)al (237 mg, 1.19 mmol, 1.4 equiv.; see Examples 17 through 19 for synthesis) was added to a suspension of HCAM resin of Example 2 or 3(1 g, 0.85 mmol) in methylene chloride (10 mL). The mixture was allowed to stir slowly for 24 hours at ambient temperature. The resin was filtered and washed with copious amounts of solvents (methylene chloride, methanol). The resin was dried under vacuum (a 2 mg portion of the resin was taken for a Kaiser Test), and then acetylated with DMF/acetic anhydride/Et$_3$N (8:1:1) for 20 minute at room temperature in order to ensure no free amine remained on the beads. Once again, the resin was dried under vacuum. Based on theoretical yield (1.15 g), Resin substitution (0.73 mmol).

EXAMPLE 10

Preparation of N$^\alpha$-Gly(Allyl)al-HydrazylCarbonyl-Amino Methylated polystyrene resin

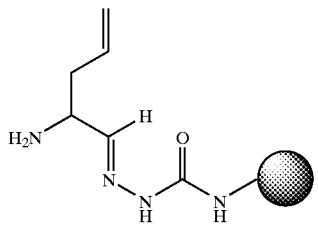

A solution of DCM/TFA/Thioanisole (6:4:1) (15 mL) was added to the resin of Example 9 (1.15 g, 0.73 mmol). The mixture was allowed to shake in a Whatman mini-column tube at ambient temperature for 25 minutes. The deprotected resin was filtered and washed with DCM (3x), DCM/DIEA (3x), and alternately with organic solvents (methylene chloride and methanol). The resulting title resin was dried under vacuum to afford 1 g resin. Kaiser Test (solution and bead; dark purple and dark brown); Resin substitution (0.79 mmol/g).

The title resin was used as starting material to synthesize a serine protease inhibitor having a glycine aldehyde as its terminal residue.

EXAMPLE 11

Preparation of N-alpha-fluorenyloxycarbonyl-omega, omega'-di-N-t-butoxycarbonyl-arginine methyl ester To a solution of N-alpha-fluorenyloxycarbonyl-omega, omega'-di-N-t-butoxycarbonyl-arginine (4.97 g, 8.329 mmol, Advanced Chemtech) in acetonitrile (82 mL) was added potassium carbonate (1.38 g, 10 mmol) and methyl iodide (1.037 mL, 16.66 mmol). The mixture was warmed to 50° C. After stirring for 4.5 hours at 50° C., the reaction mixture was poured into ethyl acetate (500 mL) and washed successively with water (1x50 mL), saturated sodium bicarbonate (1x50 mL), and brine (1x50 mL). The organic phase was dried with sodium sulfate, and solvent was removed under reduced pressure yielding 4.7 g of the title compound.

EXAMPLE 12

Preparation of N-alpha-fluorenyloxycarbonyl-omega, omega'-di-N-t-butoxycarbonyl-argininol To a solution of the compound of Example 11 (5.675 g, 9.29 mmol) in tetrahydrofuran (15.5 mL) and methanol (93 mL) was added calcium chloride(2.06 g, 18.58 mmol), and the mixture was cooled in an ice bath. Sodium borohydride (1.4 g, 37.17 mmol) was added slowly in portions to the stirred cooled solution. After 1.5 h solvent was removed under reduced pressure. The residue was suspended in ethyl acetate (500 mL) and water (30 mL). The phases were separated, and the organic layer was washed successively with 0.5M HCl (200 mL), and brine (200 mL). The combined aqueous washes were back extracted with ethyl acetate. The ethyl acetate layers were combined, silica was added (30 g), and solvent was removed under reduced pressure. This silica was loaded onto a 150x80 mm silica flash column, and the product was eluted with 50% ethyl acetate/hexanes to afford 3.855 g (71% yield) of the title compound. 0.938 g (17%) of the compound of Example 11 (starting material) was recovered. Rf=0.30 (50% ethyl acetate/hexanes). $^1$H NMR (CDCl3): 8.35 ppm(bs, 1H), 7.75 ppm(m, 2H), 7.6 ppm(m, 2H), 7.38 ppm(m, 2H), 7.3 ppm (m, 2H), 5.45 ppm(m, 1H), 4.4 ppm(d, 2H), 4.2 ppm(m, 1H), 3.7 ppm(m, 2H), 3.57 ppm(m, 1H), 3.45 ppm(m, 1H), 3.35 ppm(m, 2H), 2.15 ppm(m, 1 H), 1.6 ppm(m, 4H), 1.45 ppm(d, 18H).

EXAMPLE 13

Preparation of N-alpha-fluorenyloxycarbonyl-omega, omega'-di-N-t-butoxycarbonyl argininal hydrazonylcarbonyl aminomethylated polystyrene resin To a solution of the compound of Example 12 (3.62 g, 6.21 mmol) in methyl sulfoxide (31 mL) and toluene (31 mL) cooled in an ice bath was added EDC (11.93 g, 62.1 mmol) and dichloroacetic acid (2.56 mL, 31.06 mmol). The reaction was stirred for 40 minutes until no starting material was observed by TLC (50% ethyl acetate/hexanes). Water (150 mL) and ethyl acetate (500 mL) were added, and the phases were separated. The organic layer was then washed successively with 0.5M HCl (100 mL), saturated sodium bicarbonate (2x100 mL), and brine (100 mL). The organic layer was dried with sodium sulfate, and solvent removed under reduced pressure. This residue was then dissolved in dichloromethane (45 mL), added to the solid support of Example 2 (3.65 g, 3.1 mmol), and stirred in a sealed tube end-over-end overnight. The resin was filtered and washed successively with dichloromethane (3x50 mL), dimethylformamide (3x50 mL), and methanol (3x50 mL), and dried under high vacuum. Yield of title compound was 4.3 g. The piperidine fulvene determination of the loading showed 0.37 mmol/g (60% coupling).

EXAMPLE 14

Preparation of benzenesulfonyl-D-seryl-azetidyl-argininal, trifluoroacetate salt Step 1: omega, omega'-di-N-t-butoxycarbonyl-Argininal hydrazonylcarbonyl aminomethylated polystrene resin The resin product of Example 13, (125 mg) was treated with 30% piperidine/dimethylformamide (1.5 mL) in a 4 mL polypropylene column. After 30 min, the resin was drained, washed successively with dichloromethane (2x3 mL) and methanol (2x3 mL), and dried under vacuum to give the title compound. A ninhydrin assay on a small aliquot gave dark blue resin and solution showing a high yield for the deprotection.

Step 2: Preparation of N-α-Fmoc-azetidine-2-carbonyl-omega, omega'-di-N-t-butoxycarbonyl-argininal hydrazonylcarbonyl aminomethylated polystyrene resin:

To the compound of Step 1 (0.12 g) in a 4 mL polypropylene column were added N-α-Fmoc-azetidine-2-carboxylic acid (110 mg, 0.34 mmol), 1-hydroxybenzotriazole (7.7 mg, 0.057 mmol), TBTU (37 mg, 0.11 mmol) and diisopropylethylamine (29.8 µL, 0.17 mmol) in dimethylformamide (95 µL). The reaction mixture was shaken at room temperature overnight. The reagents were drained from the resin and the resin was washed successively with dichloromethane (2x3 mL), and methanol (2x3 mL). The resin was vacuum dried and a small aliquot was taken for ninhydrin colorimetric analysis which showed a 97% coupling efficiency in the production the title compound.

Step 3: Azetidine-2-carbonyl-omega, omega'-di-N-t-butoxycarbonyl-Argininal hydrazonylcarbonyl aminomethylated polystyrene resin The compound of Step 2 was treated with 30% piperidine/dimethylformamide (1.5 mL) in a 4 mL polypropylene column. After 30 min, the resin was drained, washed successively with dichloromethane (2×3 mL) and methanol (2×3 mL), and dried under vacuum to give the title compound. A ninhydrin assay on a small aliquot gave dark blue resin and solution showing a high yield for the deprotection.

Step 4: Preparation of N-α-Fmoc-seryl(O-t-Bu)-azetidine-2-carbonyl-N-omega, omega'-di-N-t-butoxycarbonyl-arginial hydrazonylcarbonyl aminomethylated polystyrene resin:

To the compound of Step 3 (0.12 g) in a 4 mL polypropylene column were added N-α-Fmoc-D-serine t-butyl ether (43 mg, 0.11 mmol), 1-hydroxybenzotriazole (7.7 mg, 0.057 mmol), TBTU (37 mg, 0.11 mmol) and diisopropylethylamine (29.8 μL, 0.17 mmol) in dimethylformamide (95 μL). The reaction mixture was shaken 4 h at room temperature. The reagents were drained from the resin, and the resin was washed successively with dichloromethane (2×3 mL), and methanol (2×3 mL). The resin was dried under vacuum, then double coupled using N-α-Fmoc-serine O-t-butyl ether (43 mg, 0.11 mmol), 1-hydroxybenzotriazole (7.7 mg, 0.057 mmol), TBTU (37 mg, 0.11 mmol) and diisopropylethylamine (29.8 μL, 0.17 mmol) in dimethylformamide (95 μL). The reaction mixture was shaken 2 h at room temperature. The reagents were drained from the resin, and the resin was washed successively with dichloromethane (2×3 mL), and methanol (2×3 mL). The resin was dried under vacuum, and a small aliquot was taken for ninhydrin colorimetric analysis which showed a 97.4% coupling efficiency in the production the title compound.

Step 5: Seryl(O-t-Bu)-azetidine-2-carbonyl-omega, omega'-di-N-t-butoxycarbonyl-argininal hydrazonylcarbonyl aminomethylated polystyrene resin The compound of Step 4 was treated with 30% piperidine/dimethylformamide (1.5 mL) in a 4 mL polypropylene column. After 30 min, the resin was drained, washed successively with dichloromethane (2×3 mL) and methanol (2×3 mL), and dried under vacuum to give the title compound. A ninhydrin assay on a small aliquot gave dark blue resin and solution showing a high yield for the deprotection.

Step 6: Preparation of N-α-benzenesulfonyl-D-seryl(O-t-Bu)-azetidine-2-carbonyl-omega, omega'-di-N-t-butoxycarbonyl-arginial hydrazonylcarbonyl aminomethylated polystyrene resin:

To the compound of Step 5 (0.12 g) in a 4 mL polypropylene column were added benzenesulfonyl chloride (17 μL, 0.133 mmol), and diisopropylethylamine (46.3 μL, 0.27 mmol) in dimethylformamide (888 μL). The reaction mixture was shaken overnight at room temperature. The reagents were drained from the resin, and the resin was washed successively with dichloromethane (2×3 mL), and methanol (2×3mL). The resin was dried under vacuum, then double coupled with benzenesulfonyl chloride (17 μL, 0.133 mmol), and diisopropylethylamine (46.3 μL, 0.27 mmol) in dimethylformamide (888 μL). The reaction mixture was shaken 3 h at room temperature. The reagents were drained from the resin, and the resin was washed successively with dichloromethane (2×3 mL), and methanol (2×3 mL). The resin was dried under vacuum, and a small aliquot was taken for ninhydrin colorimetric analysis which showed a 96% coupling efficiency in the production the title compound.

Step 7: benzenesulfonyl-D-seryl-azetidine-2-carbonyl-argininal, trifluoroacetate salt The compound of Step 6 (45 mg) in a 4 mL polypropylene fritted column was treated with trifluoroacetic acid/water (0.5 mL of a 9:1 mixture). The column was shaken for 1.5 h at room temperature. The reaction solution was drained into a test tube and the resin was washed with water to a total volume of 5.2 mL filtrate. The title compound was purified by semipreparative reverse-phase HPLC (0.1% trifluoroacetic acid in 0–40% aqueous acetonitrile, C-18 reverse-phase), and lyophilized to afford 14.4 g of the title compound in 26% yield. The pure fractions, as analyzed by HPLC, were combined and lyophilized to afford the title compound (2.1 mg). MS (M+H=469). The title compound demonstrates specific inhibitory activity toward urokinase. The title compound was shown to have urokinase inhibitory activity in in vitro assays.

EXAMPLE 15

Preparation of t-butoxycarbonyl-L-Arg(alloc)$_2$-ol

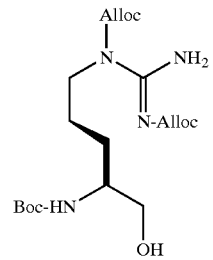

To a stirred solution of N$^a$-Boc-N$^d$-(di-Alloc)-arginine (27.97 g, 63.0 mmol; prepared according to procedure of Loffet and Zhang, 1993, Int. J. Pept. Prot. Res. 42:346–351) and triethylamine (7.65 g, 75.6 mmol, 1.2 equiv.) in anhydrous tetrahydrofuran (50 mL) at −23° C. was added dropwise a solution of isobutyl chloroformate (9.46 g, 69.3 mmol, 1.1 equiv.) in anhydrous tetrahydrofuran (13 mL) for 10 minutes under nitrogen atmosphere. The reaction mixture was warmed to 0° C. for 30 minutes. The white precipitate of triethylammonium chloride was filtered and rinsed with anhydrous tetrahydrofuran (60 mL). The filtrates and the rinses were combined and cooled to −10° C. with stirring under nitrogen atmosphere, and then NaBH$_4$ (4.29 g, 113 mmol, 1.8 equiv.) was added portionwise in 2 minutes. The reaction mixture was warmed to 0° C. for 30 minutes, and then quenched with water. The reaction mixture was acidified to pH 1 with 1N HCl and the biphasic layers were separated. The aqueous layer was extracted with ethyl acetate (2×50 mL). The combined ethyl acetate extracts and tetrahydrofuran layer were washed with brine (2×50 mL), and the crude residue was dried over sodium sulfate and filtered. Evaporation of the filtrate and purification by silica gel column chromatography using ethyl acetate/hexane 1/2 afforded the title product (16.24 g, 60.1%) as a colorless oil: R$_f$ 0.20 (methylene chloride/ethyl acetate 4/1); $^1$H (400 MHz, CDCl3): 1.4 (s, 9H), 1.6–1.8 (m, 4H), 3.6 m, 2H), 3.65(m, 1H), 4.0 (m, 2H), 4.6 (m, 4H), 5.0 (b, 1H), 5.4 (m, 4H), 6.0 (b, 2H), 9.2 (b, 1H), 9.4 (b, 1H).

EXAMPLE 16

Preparation of t-Butoxycarbonyl-L-Arg(alloc)$_2$-al

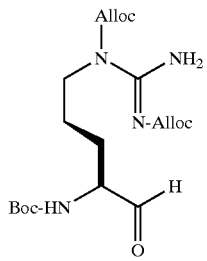

To a solution of t-butoxycarbonyl-L-Arg(alloc)$_2$-ol from Example 15 (16.24 g, 38.0 mmol) in methylene chloride (190 mL) at ambient temperature were added EDC (36.32 g, 190 mmol, 5 equiv.), dichloroacetic acid (24.5 g, 190 mmol, 5 equiv.), and dimethyl sulfoxide (26 mL). The reaction mixture was stirred for 1 h, and then quenched with water (100 mL). The solvent was removed under reduced pressure. The residue was extracted with diethyl ether (2×100 mL). The combined organic phases were washed with a 5% aqueous solution of sodium bicarbonate (250 mL), brine (250 mL), then dried over sodium sulfate and filtered. Evaporation of the filtrate afforded the title product in quantitative yield. The product was used without further purification: $R_f$ 0.57 (hexane/ethyl acetate 1/1); $^1$H (400 MHz, CDCl$_3$): 1.4 (s, 9H), 1.6–1.8 (m, 4H), 4.0 (m, 2H), 4.3 (m, 1H), 4.6 (m, 5H), 5.3 (m, 4H), 5.9–6.0 (m, 3H).

EXAMPLE 17

Preparation of t-butoxycarbonyl-L-Allyl glycine

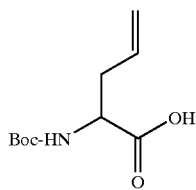

To a solution of L-Allyl glycine (25 g, 217.20 mmol, Aldrich) in acetonitrile (350 mL) was added, portion-wise, di-tert-butyl dicarbonate (61.62 g, 282.36 mmol, 1.3 equiv.), while maintaining the reaction at pH 9 to 10 by adding 1N NaOH (282 mL) dropwise. After stirring at ambient temperature overnight, the solvent was removed under reduced pressure. The crude residue was partitioned with water and hexane, and the aqueous layer was acidified to pH 3 to 4 with 1N HCl, followed by and extraction 3× with ethyl acetate solvents. The organic phases were washed 1× with 1N HCl, and 1× with H$_2$O. The residue was dried over magnesium sulfate and filtered. Evaporation of the filtrate gave 45.24 g (97% yield) of product as a white solid. $R_f$=0.34 (9 methylene chloride/1 ethanol). The desired product was judged pure by TLC. $^1$H (400 Mhz, CDCl$_3$): 1.47 (s, 9H), 2.47–2.76 (b, 2H), 4.40 (b, 1H), 5.23 (b, 1H), 5.15–5.24 (m, 2H), 5.69–5.78 (m, 1H).

EXAMPLE 18

Preparation of t-butoxycarbonyl-L-Allyl glycinyl-N-methoxy-N-methylamide

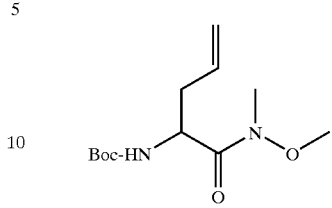

4-methylmorpholine (16.92 g, 167.36 mmol, 2.4 equiv.) was added to a solution of t-butoxycarbonyl-L-allyl glycine of Example 17 (15 g, 69.75 mmol), N,O-dimethylhydroxylamine hydrochloride (9.52 g, 97.63 mmol, 1.4 equiv.), TBTU (31.35 g, 97.63 mmol, 1.4 equiv.), and 1-hydroxybenzotriazole (13.20 g, 97.63 mmol, 1.4 equiv.) in anhydrous acetonitrile (90 mL). The reaction was stirred at ambient temperature for 16 hours and solvents were removed in vacuo. The residue was partitioned between ethyl acetate and 1N HCl. The aqueous phase was re-extracted with ethyl acetate (3×). The combined organic layers were washed with saturated sodium bicarbonate (1×), and H$_2$O (1×) and then dried over magnesium sulfate, filtered, and concentrated in vacuo. The desired product was obtained in 89% mass recovery and was judged pure by TLC. $R_f$=0.37 (1 hexane/1 ethyl acetate). $^1$H (400 Mhz, CDCl$_3$): 1.47 (s, 9H), 2.35–2.56 (bb, 2H), 3.23 (s, 3H), 3.80 (s, 3H), 4.79 (b, 1H), 5.06–5.18 (m, 2H), 5.19–5.24 (b, 1H), 5.71–5.85 (m, 1H).

EXAMPLE 19

Preparation of t-butoxycarbonyl-L-Allyl glycinal

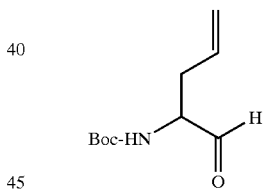

To a solution of t-butoxycarbonyl-L-Allyl glycinyl-N-methoxy-N-methylamide of Example 18 (10 g, 38.74 mmol) and anhydrous tetrahydrofuran (58 mL) in a 3 necked round bottomed flask was added dropwise 1M lithium aluminum hydride/tetrahydrofuran (58.12 mL, 1.5 equiv.) at −78° C. over 15 minutes under nitrogen atmosphere. The reaction was kept at −78° C. with stirring for 1 hr, and then allowed to stir at room temperature for 20 minutes. The reaction mixture was once again cooled to −78° C. and quenched slowly with 2M potassium bisulfate (25 mL). The solvent was removed under reduced pressure. The residue was partitioned with ethyl acetate and 1N HCl. The aqueous phase was re-extracted with ethyl acetate (3×), washed with H$_2$O (1×), saturated sodium bicarbonate (1×), and H$_2$O. The residue was dried over sodium sulfate and filtered. Evaporation of the filtrate afforded product in quantitative yield. The desired product was judged pure by TLC. $R_f$=0.33 (2 hexane/1 ethyl acetate). $^1$H (400 Mhz, CDCl$_3$): 1.47 (s, 9H), 2.40–2.66 (bb, 2H), 4.26 (d, 1H), 5.07 (d, 1H), 5.15–5.21 (m, 2H), 5.65–5.80 (m, 1H), 9.60 (s, 1H).

EXAMPLE 20

Preparation of $N^\alpha$-Fmoc-$N^d$-(di-Alloc)-Arginal-hydrazylcarbonl-amino methylated polystyrene resin

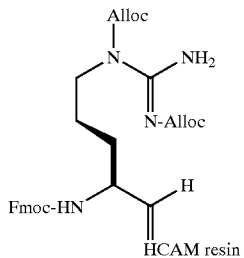

The title resin was made according to the procedures of Example 15–16 and Example 4, substituting $N^\alpha$-Fmoc-$N^d$-(di-Alloc)-arginine (Loffet and Zhang, 1993, Int. J. Pept. Prot. Res. 42:346–351) for $N^\alpha$-Boc-$N^d$-(di-Alloc)-arginine in Example 15.

EXAMPLE 21

Preparation of Libraries of Peptide or Peptidomimetic Compounds—Using the Resin of this Invention in Combinatorial Chemistry The invented solid supports also are useful in the field of combinatorial chemistry and development of chemical libraries. With reference to the following formula, it will be appreciated that preferred methods within this aspect of the invention result in the development of combinatorial libraries having an aldehyde in the P1 position, especially argininals and glycinals:

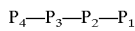

$P_4$—$P_3$—$P_2$—$P_1$

According to this aspect of the invention, a library was designed wherein the $P_1$ residue was kept constant while residues $P_4$, $P_3$, and $P_2$ were varied and incorporated into, for example, peptides and peptidomimetic $P_1$ aldehydes. Using the invented supports, multiple reactions were carried out in parallel. The $P_1$ site was first incorporated onto the resin, e.g. the HCAM resin of this invention, (see Examples 1–5), followed by incorporation of variations in the $P_4$, $P_3$, and $P_2$ residues, thereby forming a library of peptide or peptidomimetic compounds available for structure-activity analyses in any of a number of in vitro or in vivo assay systems, including protease inhibition assays.

As will be appreciated by those skilled in the art, this process of library formation and parallel synthesis may be carried out in a number of known formats. In one embodiment, the synthesis was conducted in Whatman mini columns, or the like, wherein standard peptide synthetic methods known in the art were used to extend the peptide chain, with each subsequent coupling being achieved at the carboxy terminus of each added residue. Following synthesis, the multiple peptide variants were cleaved from the resin, isolated, and tested for biological activity, as follows:

Individual members of the library were synthesized in Whatman mini columns for their carboxy terminus using standard peptide synthetic techniques. A total of 20 Whatman mini columns were used. The starting resin containing $P_1$ aldehyde was used and had the general formula: H2N—(CHR)—C=HCAM resin (50 mg resin; substitution: 0.79 mmol/g) which was weighed in each of the 20 mini columns. 1.5 mL of solvent was used in each reaction mini column at each deprotection or coupling reaction, except that 3×5 mL of solvent was used during washing steps. The standard Fmoc/tBu/Alloc protection strategy was employed and 1.5 equivalents of coupling reagents were used in each step. All coupling reactions were achieved using PyBOP/DIEA coupling reagents in DMF.

Coupling of the first residue $P_2$ to $P_1$ aldehyde was carried out at ambient temperature overnight. The mini columns were drained and washed successively with DMF, DCM, and MeOH or ether. Coupling was determined for each mini column using the quantitative Kaiser ninhydrin test. Double coupling reactions using fresh reagents were carried out when necessary. The resins were then subjected to standard Fmoc cleavage (using 20% piperidine in DMF, 30 minutes) and another round of acylation was then carried out. The cycle was continued until peptides of the desired length had been assembled.

The Whatman mini columns were then dried in vacuo. The resin in each mini column was treated with a 9:1 mixture of trifluoroacetic acid: water for one hour (1.5 mL). After draining the cleavage products into separate test tubes, the crude products were purified by Sepak column or HPLC and analyzed by mass spec and $^1$NMR spectroscopy.

EXAMPLE 22

Purification of Peptides or Proteins Using the Resin of this Invention

As disclosed herein, the novel resin of this invention provides a convenient platform for manual or automated synthesis of peptides and peptide analogs, including protease inhibitory transition state analog peptidomimetics. In a further aspect of this invention, due to the facile nucleophilic reaction that occurs between the resin of this invention and aldehyde-bearing molecules, biologically relevant molecules may be purified or isolated by exposure to the resin of this invention under acidic conditions, such that formation of a stable semicarbazone derivative is catalyzed. Subsequent washing steps removes compounds that do not bear an active aldehyde moiety. Following washing, the free aldehyde may again be released by treatment with strong acid (e.g. TFA treatment). This aspect of the invention is evident from a review of examples 3–8 hereof, wherein an argininal is contacted with a hydrazyl-carbonyl-amino methylated polystyrene resin of this invention, amino acids or amino acid analogs (protected or unprotected) are coupled to the argininal that has formed a stable semicarbazone with the resin, intermediate deprotection and further coupling steps occur, and finally, the peptide or peptide analog, including a peptidomimetic protease inhibitor is released as the free aldehyde thrombin inhibitor. Likewise for examples 11–14, which exemplify the formation of a urokinase inhibitor. However, it is not required that chemistry be conducted on the immobilized peptide or protein. In fact, essentially any compound bearing a free aldehyde or a moiety that may be easily converted to an aldehyde (e.g. a free carboxylic acid) may be purified and/or isolated according to this method. By direct analogy, the same procedure may be applied directly to the purification and/or isolation of ketoamide compounds.

EXAMPLE 23

Preparation of N-alpha-(3-phenylpropyl)-D-serine-t-butyl ether methyl ester

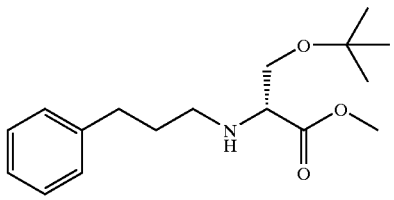

Serine O-t-butyl ether methyl ester (1.50 g, 7.1 mmol), hydrocinnamaldehyde (1.40 mL, 10.6 mmol), and triethylamine (1.18 mL, 8.5 mmol) were refluxed in tetrahydrofuran (70 mL) for 4 h. After the solution was allowed to cool to room temperature, sodium borohydride (0.46 g, 1 2 mmol) was added in two portions to the stirred solution. The reaction mixture was stirred at ambient temperature for 30 min, and the solution was concentrated under reduced pressure. The residue was partitioned between ethyl acetate 1.0M HCl. The organic layer was washed with 1.0N HCl. The aqueous layer was basified with 40% NaOH to pH 10, then extracted with ethyl acetate (2x). The combined organic layers were dried over sodium sulfate, and the solvent was removed in vacuo. The residue was purified by flash chromatography over silica gel (1x6 in column) eluting with 10–30% ethyl acetate/hexanes to afford 150 mg (7% yield) of the title compound. $R_f$=0.60 (50% ethyl acetate/hexanes).

EXAMPLE 24

Preparation of N-alpha-t-butoxycarbonyl-N-alpha-(3-phenylpropyl)-D-serine-t-butyl ether methyl ester

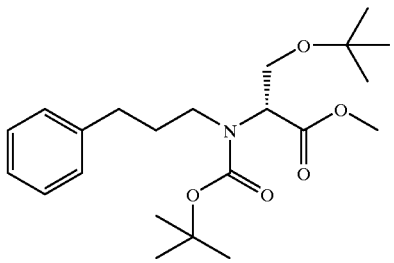

The compound of Example 23 (150 mg, 0.51 mmol), di-t-butyldicarbonate (167 mg, 0.77 mmol) and diisopropylethylamine (0.13 mL, 0.77 mmol) were stirred in tetrahydrofuran (2 mL) at ambient temperature overnight. The reaction mixture was concentrated under reduced pressure. The residue was diluted with ethyl acetate (20 mL), washed successively with 1.0N HCl 2x), saturated sodium bicarbonate (2x), and brine (1x), and the solvent was removed in vacuo to afford 206 mg of the title compound in quantitative yield. $R_f$=0.74 (50% ethyl acetate/hexanes).

EXAMPLE 25

Preparation of N-alpha-t-butoxycarbonyl-N-alpha-(3-phenylpropyl)-D-serine-t-butyl ether methyl ester

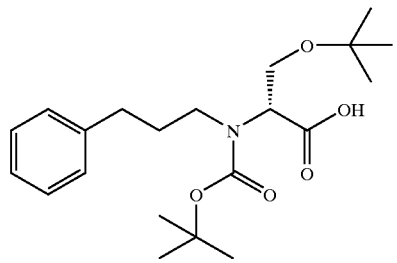

To a solution of the compound of Example 24 (206 mg, 0.52 mmol) in methanol (3.5 mL) was added dropwise 1.0N LiOH (0.63 mL, 0.63 mmol). The solution became cloudy, then became homogeneous in 5 min. The reaction mixture was allowed to stir at ambient temperature overnight. Additional 1.0N LiOH (1.47 mL) was added. After 2 h, additional 1.0N LiOH (1.0 mL) was added. After no starting material was observed by TLC (50% ethyl acetate/hexanes), the reaction mixture was acidified to pH4 with DOWEX(50X8-400) ion exchange resin. The solution was filtered, rinsing with methanol, then water. The solution was concentrated under reduced pressure, the lyophilized to afford 189 mg of the title compound in 95% yield as a yellow oil. $R_f$=0.04 (50% ethyl acetate/hexanes).

Use of the title compound according to step 4 of Example 14 (in place of N-alpha-Fmoc-D-Serine-O-t-butyl ether) results in the production of the Example 26 product, outlined below.

EXAMPLE 26

Preparation of N-alpha-(3-phenylpropyl)-D-seryl-alanyl-argininal, trifluoroacetate salt

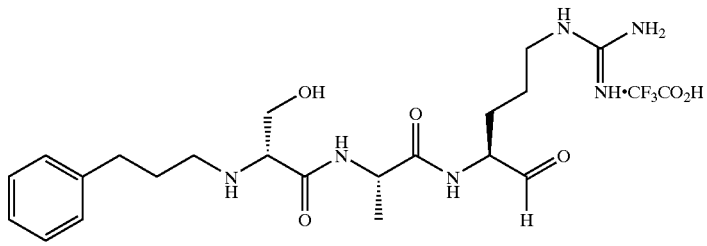

Steps 1 through 4 and Step 7 of Example 14 were followed, with the substitution in Step 2 of N-α-Fmoc-alanine for N-α-Fmoc-azetidine, and with the substitution in Step 4 of the compound of Example 25 for N-α-Fmoc-D-serine O-t-butyl ether, to make the title compound. The title compound was shown to have urokinase inhibitory activity in in vitro assays.

What is claimed is:

1. A method for production of a derivatized resin represented by formula (I):

R4-NH—(C=X)—Y—Z—SS    (I)

wherein:
R4 is —NH—R3, —NH2, —OH, or —O—R3, wherein R3 is a protecting group, provided that when R4 is —NH—R3 or —O—R3, then the protecting group is removed and replaced by —H in the final product (I);
X is O, S, or NR7;
R7 is H, alkyl, alkenyl, aryl, aralkyl, cycloalkyl, or heterocycle;
Y is absent, —NH—, or —CH2;
Z is absent or is a substituent selected from the group consisting of —NH—, —O—, —(C=O)—, —S—, SO2-, alkyl, alkenyl, aryl, aralkyl, cycloalkyl, heterocycle, provided that when Y is absent and X is O or S, Z does not comprise —(C=O)— immediately adjacent to —(C=X)—, and when Y is —NH— and Z comprises an —NH— or an —S—, at least one carbon atom separates Y and the —NH— or —S— of Z, wherein functional groups of Z are protected;
SS is a solid support;
wherein said derivatized resin represented by formula (I) is prepared by a process comprising the steps of:
(i) reacting a starting material represented by formula (C)

R1-(C=X)—Y—Z—SS,    (C)

wherein R1 is a leaving group;
with a reactant of formula (D)

R4-NH2    (D)

to form derivatized resin (I) of formula R4-NH—(C=X)—Y—Z SS; and
(ii) recovering the derivatized resin (I);
wherein said material represented by formula (C) is prepared by a process comprising the step of:
(iv) reacting a starting material of formula (A)

R—Y—Z—SS,    (A)

wherein R is a leaving group,
with a reactant of formula (B)

R1-(C=X)—R2,    (B)

wherein R2 is a leaving group, same or different than R1, to form said starting material (C) represented by formula

R1-(C=X)—Y—Z—SS.    (C)

2. The method according to claim 1 wherein R—Y of reactant (A) in step (iv) is NH2, such that said method produces a derivatized resin represented by formula (IA):

R4-NH—(C=X)—NH—Z—SS.    (IA)

3. The method according to claim 1 wherein Y is absent or is —CH₂—, and X is oxygen, such that said method produces a derivatized resin represented by formula (IB):

R4-NH—(C=O)—Y—Z—SS.    (IB)

4. The method according to claim 3 which further comprises thionating the derivatized resin (IB) to produce a product represented by formula (IC);

R4-NH—(C=S)—Y—Z—SS.    (IC)

5. The method according to claim 4 wherein said thionating comprises contacting the product (IB) with Lawesson's reagent or P2S5 in mild base.

6. The method according to claim 4 further comprising alkylating the derivatized resin (IC) with an alkylating agent capable of contributing an alkyl group R11 to form an intermediate represented by the formula (H):

R4-N=(C—S—R11)-Y—Z—SS,    (H)

and reacting the intermediate (H) with NH₂—R7 to form a product represented by the formula (ID):

R4-NH—(C=NR7)—Y—Z—SS;    (ID)

and recovering the product (ID).

7. The method according to claim 6, wherein said alkylating agent is selected from the group consisting of iodomethane, iodoethane, methylbromide, ethylbromide, allylbromide, allylchloride, dimethylsulfate, and CH3OSO3CF3.

8. The method according to claim 1 to produce a product represented by the formula (ID):

=R4-NH—(C=NR7)—Y—Z—SS    (ID)

wherein reactant (C) of step (i), when Y is not absent and R1 is —OH, is prepared by a process comprising:
reacting a starting material represented by formula (B):

R1-(C=X)—R2,    (B)

wherein R1 is —OH and R2 is an independently selected leaving group, same or different than R1, and X is NR7, with a reactant represented by formula (G):

T—Z—SS;    (G)

wherein T is —CH2Cl, —NH2, or COOH, under conditions permitting reaction of (B) with (C), such that T is transformed into moiety Y, and recovering the material (C) wherein X is NR7.

9. The method according to claim 8 wherein the reactant (B) is selected from the group consisting of diimidazole imine and phosgeneimine diimidazole.

10. The method according to claim 1 wherein, when R4 of the derivatized resin represented by formula (I) is R3-NH, R4 is converted to a derivatized resin bearing a free amine by removal of R3.

11. The method according to claim 10 wherein said derivatized resin is contacted with a protected aldehyde or ketoamide to form a semicarbazone derivatized resin.

12. The method according to claim 11 wherein said aldehyde is an argininal having a guanidino side chain and an amino terminal nitrogen.

13. The method according to claim 12 wherein said aldehyde is orthogonally protected.

14. The method according to claim 13 wherein the argininal guanidino side chain of said aldehyde is di-Boc or di-Alloc protected and said amino terminal nitrogen is Fmoc protected.

15. The method according to claim 1 wherein R1 of reagent (B) in step (iv) is selected from the group consisting of imidazole, p-nitrophenoxy, Cl, succinimidyl, and Me-imidazolium; R2 of reagent (B) of step (iv) is selected from the group consisting of imidazole, Cl, succinimidyl, and Me-imidazolium.

16. The method according to claim 1 wherein reactant (A) in step (iv) is selected from the group consisting of aminomethylated polystyrene resin and 4-methyl benzhydrylamine resin.

* * * * *